United States Patent
Klipp et al.

(10) Patent No.: US 11,742,197 B2
(45) Date of Patent: Aug. 29, 2023

(54) CLEAVABLE ADDITIVES FOR USE IN A METHOD OF MAKING A SEMICONDUCTOR SUBSTRATE

(71) Applicant: BASF SE, Ludwigshafen am Rhein (DE)

(72) Inventors: Andreas Klipp, Ludwigshafen (DE); Christian Bittner, Ludwigshafen (DE); Simon Braun, Hassloch (DE); Guenter Oetter, Ludwigshafen (DE); Yeni Burk, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 382 days.

(21) Appl. No.: 17/044,928

(22) PCT Filed: Apr. 2, 2019

(86) PCT No.: PCT/EP2019/058247
§ 371 (c)(1),
(2) Date: Oct. 2, 2020

(87) PCT Pub. No.: WO2019/192990
PCT Pub. Date: Oct. 10, 2019

(65) Prior Publication Data
US 2021/0166934 A1  Jun. 3, 2021

(30) Foreign Application Priority Data
Apr. 4, 2018 (EP) .................................. 18165603

(51) Int. Cl.
*H01L 21/02* (2006.01)
*C07C 271/12* (2006.01)

(52) U.S. Cl.
CPC ...... *H01L 21/02057* (2013.01); *C07C 271/12* (2013.01)

(58) Field of Classification Search
None
See application file for complete search history.

(56) References Cited

U.S. PATENT DOCUMENTS

| 5,868,821 | A | 2/1999 | Torii et al. |
| 6,331,566 | B1 | 12/2001 | Conrow et al. |
| 7,022,861 | B1 | 4/2006 | McElhanon et al. |
| 2001/0051648 | A1 | 12/2001 | Conrow et al. |
| 2002/0002196 | A1 | 1/2002 | Conrow et al. |
| 2006/0264020 | A1 | 11/2006 | Lazovsky et al. |
| 2011/0021015 | A1 | 1/2011 | Lazovsky et al. |
| 2012/0258595 | A1 | 10/2012 | Lazovsky et al. |
| 2013/0072026 | A1 | 3/2013 | Lazovsky et al. |
| 2013/0217238 | A1 | 8/2013 | Boussie et al. |

FOREIGN PATENT DOCUMENTS

| EP | 1 227 809 A2 | 8/2002 |
| WO | WO 95/08529 A1 | 3/1995 |
| WO | WO 01/34129 A2 | 5/2001 |
| WO | WO 02/097393 A2 | 12/2002 |
| WO | WO 2009/048611 A2 | 4/2009 |

OTHER PUBLICATIONS

International Search Report dated Apr. 24, 2019 in PCT/EP2019/058247 filed on Apr. 2, 2019, 2 pages.
Ahner et al., "Wetting Behavior of Plasma Etch Residue Removal Solutions on Plasma Damaged and Repaired Porous ULK Dielectrics", Abstract Only, Solid State Phenomena, vol. 219, Trans Tech Publications, Ltd., Sep. 2014, pp. 193-196. Crossref, doi:10.4028/www.scientific.net/ssp.219.193.
Kesters et al., "Post Etch Residue Removal and Material Compatibility in BEOL Using Formulated Chemistries", Abstract Only, Solid State Phenomena, vol. 219, Trans Tech Publications, Ltd., Sep. 2014, pp. 201-204. Crossref, doi:10.4028/www.scientific.net/ssp.219.201.
Tehrani-Bagha et al., "Cleavable surfactants", Abstract Only, Current Opinion in Colloid Interface Science, vol. 12, Issue 2, 2007, pp. 81-91, ISSN 1359-0294, https://doi.org/10.1016/j.cocis.2007.05.006.

*Primary Examiner* — Eric W Golightly
*Assistant Examiner* — Arlyn I Rivera-Cordero
(74) *Attorney, Agent, or Firm* — Armstrong Teasdale LLP

(57) ABSTRACT

The use of an organic compound as cleavable additive, preferably as cleavable surfactant, in the modification and/or treatment of at least one surface of a semiconductor substrate is described. Moreover, it is described a method of making a semiconductor substrate, comprising contacting at least one surface thereof with an organic compound, or with a composition comprising it, to treat or modify said surface, cleaving said organic compound into a set of fragments and removing said set of fragments from the contacted surface. More in particular, a method of cleaning or rinsing a semiconductor substrate or an intermediate semiconductor substrate is described. In addition, a compound is described which is suitable for the uses and methods pointed out above and which preferably is a cleavable surfactant.

8 Claims, No Drawings

CLEAVABLE ADDITIVES FOR USE IN A METHOD OF MAKING A SEMICONDUCTOR SUBSTRATE

CROSS-REFERENCE TO RELATED APPLICATIONS

This application is a is a U.S. National Phase Application of International Patent Application No. PCT/EP2019/058247, filed Apr. 2, 2019, which claims priority to European Patent Application No. 18165603.4, filed Apr. 4, 2018, the entire contents of which are hereby incorporated by reference herein.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable

STATEMENT REGARDING PRIOR DISCLOSURES BY THE INVENTOR OR A JOINT INVENTOR

Not applicable

BACKGROUND OF THE INVENTION

Field of the Invention

The present invention relates to the use of an organic compound or a salt thereof as cleavable additive, preferably as cleavable surfactant, in the modification and/or treatment of at least one surface of a semiconductor substrate. The invention also relates to a method of making a semiconductor substrate, comprising contacting at least one surface thereof with an organic compound or a salt thereof, which is a cleavable additive, so that said surface is modified or treated, cleaving said organic compound into a set of fragments and preferably removing said set of fragments from the contacted surface. More in particular, the invention also relates to a method of cleaning or rinsing a semiconductor substrate or an intermediate semiconductor substrate, comprising a step of removing at least an amount of an organic compound, preferably a cleavable surfactant, together with one or more materials from the surface of said substrate. Likewise, the invention relates to a composition comprising said organic compound as cleavable additive, for the uses and methods according to the invention. Moreover, the present invention pertains to a compound which is suitable for the uses and methods according to the invention and preferably is a cleavable additive, more preferably a cleavable surfactant.

A process for manufacturing a semiconductor substrate is a multiple-step sequence of photolithographic and chemical processing steps during which electronic circuits or microelectronic devices are gradually created on a wafer made of pure semiconducting material (a "semiconductor wafer"). Preferably, silicon is used as the semiconductor material, but various semiconductor materials are known and applied for specialized applications. The entire manufacturing process, from its start to packaged "chips" ready for use in electrical and electronic devices, takes six to eight weeks and is performed in highly specialized facilities. A typical semiconductor wafer is made of extremely pure silicon that is grown into mono-crystalline cylindrical ingots (boules) up to 300 mm in diameter using the so-called "Czochralski process". The semiconductor wafers are usually further purified by the so-called "float zone process" before these ingots are sliced into wafers about 0.75 mm thick and polished to obtain a very regular and flat surface.

The particular process for manufacturing a semiconductor substrate is structured in several phases, comprising e.g. the so-called "front-end-of-line" ("FEOL") and "back-end-of-line" ("BEOL") processing phases.

The FEOL processing phase refers to the formation of transistors on a semiconductor's surface. The raw semiconductor wafer is engineered by the growth of an ultrapure, virtually defect-free silicon layer through epitaxy. Front-end surface engineering is followed by growth of the gate dielectric (usually a high-k material like $HfSiO_x$), patterning of the gate, implanting of the source and drain regions, and subsequent formation of the contact region.

Once the various semiconductor devices have been created, they must be interconnected to form desired electrical circuits or microelectronic devices. This occurs in a series of wafer processing steps collectively referred to as BEOL. The BEOL processing phase involves creating metal interconnecting wires on the semiconductor wafer's surface, that are isolated by layers made of material with a low or "ultra-low" dielectric constant.

This insulating material has traditionally been a form of $SiO_2$ or a silicate glass, but today, low dielectric constant materials (also often referred to as "low-k materials") are being used to further improve performance, e.g. silicon oxycarbide, typically providing dielectric constants around 2.7 (compared to 3.82 for $SiO_2$), but materials with constants as low as 2.0 or below are also known.

Lower dielectric constant values ("k-values") have resulted in dielectric materials with higher porosity and lower density. As porosity increases, the internal pore-structure of the dielectric matrix can become more interconnected. This high porosity combined with interconnected pore volume can allow non-insulating materials, in particular copper, to diffuse or penetrate through low k-value dielectric materials. Accordingly, defects and failure mechanisms can result, which can degrade performance, reduce the operational lifetime of devices, and even lead to complete device failure. Methods have therefore recently been discussed to reduce the porosity of low-k dielectric materials, e.g. by so-called "pore-sealing" processes which involve e.g. adsorbing or depositing suitable chemical reagents on the low-k dielectric materials for closing or filling its pores.

Another known problem with porous low k-value dielectric materials due to the high porosity and low density of the materials is that they tend to have irregular or non-smooth sidewalls after features such as trenches or so-called "vias" (abbreviation for "vertical interconnect access") have been etched into them. As a consequence, subsequently formed and/or deposited materials can form irregularly along sidewalls of the low k-value dielectric layers. Thus, for example, forming copper diffusion barrier layers with a uniform thickness along sidewalls of low k-value dielectric layers can be problematic due to the irregularities of the low k-value dielectric layer sidewalls. Currently, repair processes, known as "low-k repair" or "repair of low electric constant materials", and mainly based on silylation, are therefore considered for following a previous patterning step, to reintegrate carbon-rich species and recover the dielectric's properties (see e.g. N. Ahner et al., Solid State Phenomena 219 (2015) 193-196).

As critical dimensions in manufacturing of semiconductor substrates, in particular of semiconductor wafers, continue to shrink, the impact of corrosion on metal features in BEOL integrated circuits ("IC"s) has become a concern. E.g. copper is a metal with many advantages when introduced as a metal interconnect in ICs to enhance performance, but the use of copper has also introduced problems such as the tendency to corrode if not treated properly. This is because copper does not develop native oxide corrosion protection as readily as e.g. aluminium. Corrosion that once occurred unnoticed can have widespread effects in IC performance. A common type of corrosion that can occur in BEOL wet processing is often the result of the interaction between process chemical and ultrapure de-ionized rinse water. The use of corrosion inhibitors in rinse bathes has therefore been discussed as a possibility to eliminate the need for additional intermediate solvent rinses as are commonly used to reduce this type of corrosion.

As the number of interconnect levels increases, planarization of the previous layers is required to ensure a flat surface prior to subsequent lithography. Without it, the levels would become increasingly crooked, extending outside the depth of focus of available lithography, and thus interfering with the ability to pattern. "CMP" (chemical-mechanical planarization or chemical-mechanical polishing) is the primary processing method to achieve such planarization.

Modern electronic chips have up to eleven metal levels produced in over 1000 sequenced processing steps. In a process for manufacturing a semiconductor substrate, in particular a semiconductor wafer, the various processing steps can be grouped into four general categories: deposition, removal, patterning, and modification of electrical properties.

Deposition is any process that grows, coats, or otherwise transfers a material onto the semiconductor wafer. Available technologies include physical vapor deposition ("PVD"), chemical vapour deposition ("CVD"), electrochemical deposition ("ECD"), molecular beam epitaxy ("MBE") and more recently, atomic layer deposition ("ALD"), among others.

Removal in this regard means any process that removes material from the wafer; examples include etch processes (either wet or dry) and CMP.

Patterning in this regard means the shaping or altering of deposited materials, and generally includes a stop of lithography. For example, in conventional lithography, a semiconductor wafer is coated with a photoresist; then, a so-called "stepper" machine focuses, aligns, and moves an inert mask (reticle), exposing select portions of the semiconductor wafer below to short wavelength light; the exposed or unexposed regions of the photoresist (depending on the use of positive or negative photoresists, respectively) are washed away by a developer solution. After etching or other processing, the remaining photoresist is removed by a process called "plasma ashing". Residuals from plasma ashing often need to be removed in a separate working step, usually by cleaning solutions ("wet chemicals") which are often specifically designed for a certain wet cleaning step.

Modification of electrical properties has historically entailed doping transistor sources and drains, originally by diffusion furnaces and later by ion implantation. These doping processes are followed by furnace annealing or, in advanced devices, by rapid thermal annealing ("RTA"); annealing serves to activate the implanted dopants. Modification of electrical properties now also extends to the reduction of a material's dielectric constant in low-k material insulators via exposure to ultraviolet light in UV processing ("UVP") and the release of "porogens" from the low-k material. Porogens are generally any of a mass of particles (usually of a specified shape and size) used to make pores in solid, e.g. moulded, structures used for structure-engineering and are usually dissolved, cleaned or rinsed away after the structure has set.

In most of these processing step categories, chemical additives are used for different purposes of modifying and/or treating the surface of a semiconductor substrate, in particular a semiconductor wafer or an intermediate for producing a semiconductor substrate. In particular, chemical additives, especially surfactants, are applied before and/or after one or more processing steps from said processing step categories to prepare a surface of a semiconductor substrate, in particular a semiconductor wafer, for the next processing step and/or for finishing a processing phase or production as a whole.

The wet chemical processing of small pattern on a semiconductor substrate, in particular on a semiconductor wafer, involves a plurality of problems, including problems of removing process chemicals and/or working liquids and/or working fluids after their use.

As technologies advance and dimension requirements become stricter, photoresist patterns are required to include relatively thin and tall structures or features of photoresists, i.e., features having a high aspect ratio, on the substrate. These structures may suffer from bending and/or collapsing (known as the phenomenon of "pattern collapse"), in particular, during cleaning or rinsing processes, due to excessive capillary forces of the liquid or solution remaining from the cleaning or rinsing solution between adjacent photoresist features, in particular during the spin dry processes. The maximum stress ($\sigma$) between small features caused by the capillary forces can e.g. be lowered by decreasing the surface tension $\gamma$ of the cleaning or rinsing fluid (both dynamic and equilibrium surface tension). In order to decrease the surface tension of a fluid or a liquid, surfactants are usually added to said fluid or liquid.

Another problem of the conventional photolithographic process is line edge roughness ("LER") and line width roughness ("LWR") due to resist and optical resolution limits. LER includes horizontal and vertical deviations from the feature's ideal form. In particular, as critical dimensions shrink the LER becomes more problematic and has negative effects, such as an increased transistor leakage current, thus lowering the performance of the IC device.

Due to the shrinkage of the dimensions of semiconductor substrates, in particular semiconductor wafers, the removal of particles becomes a critical factor to achieve a defect reduction. The latter also applies to photoresist patterns as well as to other patterned material layers, which are generated during the manufacture of semiconductor substrates, optical devices and mechanical precision devices.

An additional problem of the conventional photolithographic process is the presence of watermark defects. Watermarks may form on the photoresist as the deionized water or defect rinse solution cannot be spun off from the hydrophobic surface of the photoresist. The watermarks have a harmful effect on yield and IC device performance.

Yet another problem is the occurrence of so called "blob defects". These defects are caused during UV exposure and/or photoresist development and have often the form of a round "crater-like" opening on one or more of the top layers on the photoresist, e.g. polymeric and photosensitive layers. Small particles or other insoluble matter can be trapped in those opening and result in inefficient particle removal or blocking of the openings. In particular, hydrophobic fragments or aggregates of hydrophobic molecules can be absorbed in or on those defect sides. These remaining particles, fragments or aggregates cause problems at a later process stage.

Another problem of the conventional photolithographic process is the absorbance of solvents by the photoresist layer or the patterned material layer resulting in swelling of these layers. Patterns in very close proximity, in particular patterns having line-space structures with a line width of 50 nm or below, thus get into direct contact with each other after swelling. Furthermore, the swollen patterns in direct contact to each other will subsequently stick together even after developing, cleaning or rinsing of the product, in particular products according to the present invention. Photoresist swelling thus limits the minimum achievable line-space dimensions of a product, in particular for products according to the present invention.

As explained above, common processes for manufacturing semiconductor substrates, preferably semiconductor wafers, are multiple-step sequences of photolithographic and chemical processing steps, involving modification and treatment of surfaces of said semiconductor substrates, in particular of semiconductor wafers. Usually for each separate processing step, the surface to be processed has to be properly prepared and in particular all traces, e.g. residuals, particles or fluids from previous processing steps need to be removed. The same is true for all chemical additives, process chemicals, working fluids and/or working liquids (e.g. from defect reduction rinses, see below), which may have been used during said previous processing steps, including e.g. any surfactants used.

In order to facilitate and/or expedite processing of a semiconductor substrate, e.g. by reducing the necessary number of process steps and/or by reducing turnover times per processing step, it is therefore desirable that also process chemicals, e.g. chemical additives, working fluids and/or working liquids are conveniently, quickly, easily and where no longer-term or permanent exposure of the surface of a semiconductor substrate to the chemical additives is required or beneficial—preferably also completely removed, once they have served their purposes of modifying and/or treating the semiconductor substrate's surface and/or before the next or subsequent processing step is initiated.

Reducing processing times is not only an economic but often also a technical requirement, e.g. where sensitive layers are applied on a semiconductor wafer which may not be exposed to the processing environment for extended time periods.

However, with currently available technologies, removal, preferably complete removal, of residuals like process chemicals or chemical additives, including surfactants, after their use or application on a semiconductor substrate is often a technical challenge.

DESCRIPTION OF RELATED ART INCLUDING INFORMATION DISCLOSED UNDER 37 CFR 1.97 AND 1.98

Different teachings regarding such methods or compounds have been reported in the patent literature:

Document U.S. Pat. No. 7,022,861 describes cleavable surfactants which contain thermally labile Diels-Alder adducts.

Document WO 2009/048611 describes certain cleavable surfactant compounds, which can be used in methods for aiding the solubilisation, digestion, preparation, analysis, and/or characterization of biological material, for example, proteins or cell membranes.

Document WO 02/097393 describes cleavable surfactants and their uses in MALDI MS analysis of hydrophobic proteins.

Document WO 95/08529 describes chiral surfactants and methods for their use in chiral separations.

Document U.S. Pat. No. 5,868,821 describes a thermally reversible color forming composition and a respective thermally reversible recording medium, including certain electron-accepting carboxylic acids.

RELATED ART IS ALSO

Document US 2013/0217238 A1 deals with substrate processing including a masking layer.

Document US 2006/264020 A1 describes the formation of a masking layer on a dielectric region to facilitate formation of a capping layer on electrically conductive regions separated by the dielectric region.

BRIEF SUMMARY OF THE INVENTION

Not applicable

BRIEF DESCRIPTION OF THE SEVERAL VIEWS OF THE DRAWING(S)

Not applicable

DETAILED DESCRIPTION OF THE INVENTION

In view of the foregoing, it was a primary object of the present invention to provide an organic compound for the use as cleavable additive in the modification or treatment of at least one surface of a semiconductor substrate, in particular a semiconductor wafer, which cleavable additive can be conveniently, quickly, easily and, where required or beneficial, also completely removed.

It was another object of the present invention to provide a method of making a semiconductor substrate, in particular a semiconductor wafer, comprising contacting at least one surface of the semiconductor substrate with said organic compound, preferably a cleavable additive, so that said surface is modified or treated and the cleavable additive can subsequently be conveniently, quickly, easily and preferably completely removed.

It was a more specific object of present invention to provide a method of cleaning and/or rinsing a semiconductor substrate, in particular a semiconductor wafer or an intermediate semiconductor wafer, for producing a cleaned and/or rinsed semiconductor substrate, the method involving said organic compound, which preferably is a cleavable surfactant.

It was another object of the present invention to provide an organic compound which is suitable as cleavable additive, in particular as cleavable surfactant, in the modification and/or treatment of at least one surface of a semiconductor substrate, in particular of a semiconductor wafer.

The invention as well as preferred variants and preferred combinations of parameters, properties and elements thereof are defined in the appended claims. Preferred aspects of the present invention are furthermore defined in the following description and in the examples stated below.

It has now been found that the primary object and other objects of the invention are accomplished by a use of an organic compound of formula I

A-L-B  (I), or a salt thereof, wherein
A is a tail group,
B is a head group and
L is a linking group,
as cleavable additive in the modification and/or treatment of at least one surface of a semiconductor substrate,
where the compound of formula I is cleaved into a set of fragments subsequent to said modification or treatment, for facilitating its removal from said surface.

In the context of the present invention a "semiconductor substrate" comprises a semiconductor wafer, from the beginning of its production (i.e. a blank, untreated, uncoated and unpatterned semiconductor wafer, also referred to as a "start semiconductor wafer" in this text) throughout all its processing steps (including all processing steps in FEOL and BEOL processing phases, as explained above; also referred to as an "intermediate semiconductor wafer" in this text) until and including the completion of its processing. Upon completion of the processing of a semiconductor wafer, a "microelectronic device" results which is preferably situated on at least one surface of a semiconductor wafer. Such microelectronic device is also comprised by the term "semiconductor substrate" as used in the context of the present invention.

In the context of the present invention and consistent with the usual understanding in the technical field, a microelectronic device is preferably selected from the group consisting of transistors, capacitors, inductors, resistors, diodes, insulators and conductors. A plurality of microelectronic devices can form one or more integrated circuits.

A semiconductor wafer according to the present invention comprises or consists of a semi-conductive material, preferably silicon. Preferably, the at least one surface of a semiconductor wafer to be modified or treated comprises one or more materials selected from the group consisting of a metal nitride, preferably TiN; and an oxide of Si, preferably HfSiOx, SiOC(N) and $SiO_2$, more preferably crystalline $SiO_2$.

During processing of a semiconductor substrate or a semiconductor wafer (the semiconductor wafer during its processing phases also being referred to as an "intermediate semiconductor wafer"), several coatings of different materials are usually applied to at least one of its surfaces as explained above, e.g. coatings of one or more photoresist layers, one or more protective layers (e.g. etch stop layers), one or more insulating layers (e.g. layers of low electric constant insulating material, also known as low-k material) and/or one or more functional layers. Immediately after its application, a coating or layer is usually unpatterned. Subsequently, the coating or layer, in particular a functional coating, can be patterned (or structured) by processes known in the art, as also explained above. Where a semiconductor wafer has patterns or structures on at least one of its surfaces is also referred to in this text as "patterned semiconductor wafer" or "structured semiconductor wafer", respectively. The term "intermediate semiconductor wafer" as used in this text comprises such patterned semiconductor wafers and structured semiconductor wafers.

A semiconductor substrate, in particular a semiconductor wafer, in the context of the present invention and consistent with the usual understanding in the technical field, is preferably macroscopically planar, i.e. the layers, patterns or structures on at least one of the semiconductor substrate's or semiconductor wafer's surfaces are not higher than 5 µm (i.e. not extending more than 5 µm in height in a perpendicular direction to the surface of the semiconductor substrate or the semiconductor wafer).

A cleavable additive in the context of the present invention is an organic compound of formula I which comprises two groups, a tail group A and a head group B, which groups are linked by a linking group L. Preferably, L is bonded via covalent bonds to any of A and B.

The groups A and B are chemical groups comprising functional groups which are suitable for having an effect in the modification or treatment of at least one surface of a semiconductor substrate. Preferably, the groups A and B are different and/or are adapted according to the particular purpose of modification and/or treatment of the at least one surface of a semiconductor substrate, as further explained below.

In a preferred variant of the invention, the use of the compound of formula I as cleavable additive is a use as cleavable surfactant. In the context of the present invention, a "cleavable surfactant" is—consistent with the usual understanding in the technical field—an amphiphile in which a "weak linkage" has been deliberately inserted, usually between a hydrophobic tail group and a polar head group. For the use according to the invention, the tail group A is preferred as hydrophobic tail group and the head group B is preferred as polar head group, both as defined in detail in this text. The term "cleavable surfactant" is established in the field and is commonly used for the type of compounds as explained here before; for reference see e.g. documents U.S. Pat. No. 7,022,861; WO 2009/048611 or WO 02/097393, or the review article by A. Tehrani-Bagha et al., Current Opinion in Colloid & Interface Science, Vol. 12 Is. 2 (2007) 81-91.

In particular, in the preferred variant of the invention where the use of the compound of formula I is as cleavable surfactant (as explained in more detail below), the tail group A is preferably a hydrophobic group, more preferably a straight-chain or branched $C_4$-$C_{20}$-alkyl group, which is substituted by 1 to 4 ether groups or is preferably unsubstituted. Yet more preferably, in this preferred variant, A is a straight-chain or branched aliphatic hydrocarbon group having a total number of 4 to 20, preferably of 6 to 16, carbon atoms, which is substituted by 1 to 4 ether groups or is preferably unsubstituted. Most preferably, in this preferred variant, A is a monovalent group "$R^1$—$CH_2$—", where $R^1$ is a straight-chain or branched aliphatic hydrocarbon group having a total number of 4 to 20, preferably of 6 to 16, more preferably of 7 to 14, still more preferably of 7 to 12, carbon atoms.

In particular in the preferred variant of the invention where the use of the compound of formula I is as cleavable surfactant, the head group B is preferably a polar group, preferably comprising in its chemical structure at least one ionic group independently selected from anionic groups, preferably carboxylate, sulfate, sulfonate or phosphate, more preferably carboxylate; and cationic groups, preferably ammonium which is unsubstituted or substituted by 1 to 3 straight-chain or branched $C_1$-$C_4$-alkyl groups ("alkyl ammonium"). More preferably, in this preferred variant, B is a straight-chain or branched aliphatic hydrocarbon group having a total number of 1 to 6, preferably of 1 to 4, carbon atoms, which is substituted by one or two, preferably by one, ionic group independently selected from anionic groups, preferably carboxylate, sulfate, sulfonate or phosphate; and cationic groups, preferably ammonium which is unsubstituted or substituted by 1 to 3 straight-chain or branched $C_1$-$C_4$-alkyl groups. Most preferably, in this preferred variant, B is a monovalent ionic group of formula II

(II)

where $R^2$ is a straight-chain or branched aliphatic hydrocarbon group having a total number of 1 to 6, preferably of 1 to 4, carbon atoms and $Y^+$ is a singly charged ammonium cation which is unsubstituted ("ammonium cation") or substituted ("alkyl ammonium cation") by 1 to 3 $C_1$-$C_4$-alkyl groups; and preferably $Y^+$ is unsubstituted ammonium.

The linking group L comprises or represents (preferably represents) a bond or a chemical group which in each case is selectively cleaved or rearranged when induced by at least one suitable trigger or triggering event selectively acting upon the linking group L, to release a set of fragments from the compound of formula I. "Selectively acting on" preferably means that said trigger or triggering event does not directly impact the fragments A and B or their chemical structures, apart from releasing them from the compound of formula I (i.e. not directly impact the chemical structures of the fragments A and B which are not involved in the binding to the fragments A or B) due to the action of said trigger or triggering event on L. Selective cleavage or rearrangement of the linking group L preferably results in a controlled and selective cleavage of the cleavable additive (the compound of formula I) into a set of fragments. As said fragments are smaller than the compound of formula I, they can usually be easier removed from a surface, preferably from a surface of a semiconductor substrate, than said un-decomposed compound of formula I. Preferably, L is bonded via covalent bonds to any of A and B.

In preferred variants of all aspects of the present invention (uses, method of making, method of cleaning and/or rinsing, and compound), preferably in the preferred variants where the compound of formula I is a cleavable surfactant, the linking group L is a (divalent) urethane group "—N(H)—C(O)O—". In one variant of these preferred variants, the linking group L can link the group A, preferably a preferred group A as defined above, via the nitrogen atom and the group B, preferably a preferred group B as defined above, via the oxygen atom of the carboxyl group (thus creating a structure "A-N(H)—C(O)O—B"). In another variant of these preferred variants, the linking group L can link the group A via the oxygen atom of the carboxyl group and the group B via the nitrogen atom (thus creating a structure "B—N(H)—C(O)O-A"). The variant where the linking group L links the group A via the nitrogen atom and the group B via the oxygen atom of the carboxyl group is preferred with respect to all aspects of the present invention.

Preferably, the compound of formula I or its salt has a molecular weight not exceeding 1500 g/mol, more preferably not exceeding 1000 g/mol. Unlike a polymer, the compound of formula I or its salt does not solely consist of a plurality of identical (monomeric) units.

"Modification" of at least one surface of a semiconductor substrate in the context of the present invention preferably means that after a certain process step in a method of making a semiconductor substrate or a microelectronic device, upon contacting said at least one surface of said semiconductor substrate, preferably of a semiconductor wafer, more preferably of an intermediate semiconductor wafer, a cleavable additive exerts its effect on said surface and subsequent to exerting said effect, it is cleaved into a set of fragments. Said fragments are subsequently removed, preferably at least partially removed from said surface. Partial removal of said fragments from said surface, where required or beneficial, has the effect that at least a part of said fragments may remain on said surface and may exert a longer-lasting or permanent effect on said surface. Preferred processes comprising modification or modifying said at least one surface of a semiconductor substrate, preferably a semiconductor wafer, are selected from the group consisting of pore-sealing of low-k dielectric materials, repairing films of low-k dielectric materials, changing the zeta-potential of at least one surface of the semiconductor substrate, changing the contact angle on at least one surface of the semiconductor substrate, changing the adsorption or adhesion properties of at least one surface of the semiconductor substrate in relation to the compound of formula I and inhibiting corrosion of corrosion-sensitive materials, preferably selected from the group consisting of copper, cobalt and tungsten, more preferably inhibiting corrosion of copper, as explained above.

"Treatment" of at least one surface of a semiconductor substrate in the context of the present invention preferably means treating the at least one surface of an intermediate semiconductor substrate, preferably of a semiconductor wafer, more preferably of an intermediate semiconductor wafer, in a way that a cleavable additive, upon contacting said at least one surface, exerts its effect on said surface and subsequent to exerting said effect, it is cleaved into a set of fragments, preferably upon a trigger or triggering event. Said fragments are subsequently removed, preferably completely removed, from said surface. Preferred processes comprising treatment or treating said at least one surface of a semiconductor substrate, preferably a semiconductor wafer, are cleaning and rinsing. Most preferred according to the invention as "treatment" is cleaning.

"Cleaning" of at least one surface of a semiconductor substrate in the context of the present invention preferably means cleaning at least one surface of a semiconductor substrate, preferably of a semiconductor wafer, more preferably of an intermediate semiconductor wafer, from residuals or remainders of previous processing steps, preferably by removing particles, pieces or fragments of photoresist or other layers, which may have formed as a result of previous processing steps of e.g. FEOL or BEOL processes (also referred to as "contaminations" in the present text), e.g. removal of post-etch residues (for reference see e.g. E. Kester et al., Solid State Phenomena 219 (2015) 201-204) e.g. etch plasma residuals as occurring in dry-etching processes like ions, metal traces and their nitrides, oxides and/or fluorides. The cleaning need of the semiconductor substrate's surface can occur at different stages of the process for manufacturing a semiconductor substrate, preferably a microelectronic device, in particular after production of a semiconductor crystal and before any FEOL processing phase, at several stages during, and after the FEOL processing phase and before, at different stages during, and after the BEOL processing phase. The term "cleaning" in the context of the present invention as explained above also comprises steps where remainders of previous processing steps, preferably particles, pieces or fragments of photoresist or other layers, which may have formed as a result of previous processing steps of e.g. FEOL or BEOL processes, are "rinsed" or rinsed off from at least one surface of a semiconductor substrate. In particular, the term "cleaning" in the context of the present invention comprises defect reduction rinses (see below), post-ash residue removal rinses, post-etch residue removal rinses and photoresist residue removal rinses.

"Rinsing" of at least one surface of a semiconductor substrate in the context of the present invention preferably means rinsing the surface of a semiconductor substrate, preferably of a semiconductor wafer, more preferably of an intermediate semiconductor wafer, to remove any working fluids or working liquids which may be present from previous processing steps and/or to prepare the semiconductor wafer for drying after a rinsing step. The rinsing need of the semiconductor substrate's surface can occur at different stages of the process for manufacturing a semiconductor substrate, preferably a microelectronic device, in particular after production of a semiconductor crystal and before any FEOL processing phase, at several stages during, and after the FEOL processing phase and before and at different stages during, and after the BEOL processing phase.

Cleaning and/or rinsing steps according to the present invention are preferably to be conducted in a way so as to preserve the surface structure of the semiconductor substrate in its particular processing status, e.g. in the status as plain semiconductor wafer before entering the FEOL processing steps (a "start semiconductor wafer") or subsequently in the status as patterned or unpatterned semiconductor wafer comprising one or more patterned or unpatterned layers of e.g. photoresist, insulator (e.g. low k-value) materials and/or metals (an "intermediate semiconductor wafer"). More preferably, cleaning and/or rinsing steps are to be conducted in a way so as to preserve any patterns or structures already present on the semiconductor substrate's or semiconductor wafer's surface or in one or more layers present on said surface and thus preferably prevent, avoid and/or reduce the undesired phenomena often occurring with photolithographic processes, in particular pattern collapse, line edge roughness, water mark defects, photoresist-swelling and/or blob-defects, where cleaning and/or rinsing steps which prevent, avoid and/or reduce said undesired phenomena are also known and collectively referred to in the context of the present invention as "defect reduction rinses".

Preferred is a use according to the invention, wherein
said semiconductor substrate is selected from the group consisting of
a semiconductor wafer,
an intermediate semiconductor wafer and
a microelectronic device,
and/or
said modification is selected from the group consisting of pore-sealing of low-k dielectric materials, repairing films of low-k dielectric materials, changing the zeta-potential of at least one surface of the semiconductor substrate, changing the contact angle on at least one surface of the semiconductor substrate, changing the adsorption or adhesion properties of at least one surface of the semiconductor substrate in relation to the compound of formula I and inhibiting corrosion;
and/or
said treatment is selected from the group consisting of cleaning and rinsing.

Preferred is also a use according to the present invention (or a use according to the present invention which is designated as being preferred in this text) wherein said modification and/or treatment is or comprises (preferably "is") cleaning and/or rinsing and preferably comprises defect reduction rinses, post-ash residue removal rinses, post-etch residue removal rinses and photoresist residue removal rinses.

Further preferred is a use according to the invention (or a use according to the present invention which is designated as being preferred in this text), wherein
cleaving of said compound of formula I is induced by at least one trigger, independently selected from the group consisting of a chemical reaction, preferably pH change, reduction, oxidation, nucleophilic attack, electrophilic attack and enzymatic cleavage; and application of energy, preferably heat and/or irradiation,
and/or
said removal is done by at least one process selected from the group consisting of evaporation, sublimation, rinsing, hydrolysis and dissolution,
and more preferably said removal is done by evaporation.

In the context of the present invention, a use of a compound of formula I is preferred in the treatment of at least one surface of a semiconductor substrate, preferably in the cleaning and/or rinsing of at least one surface of a semiconductor substrate, more preferably in the cleaning and/or rinsing of at least one surface of a semiconductor wafer, yet more preferably in the cleaning or rinsing of at least one surface of an intermediate semiconductor wafer. In this preferred variant, the use of said compound of formula I preferably is as cleavable surfactant (as explained in more detail below).

According to the present invention, cleaving of said compound of formula I is preferably induced by at least one trigger or triggering event (as stated above). The suitable or applicable trigger (or triggering event) and thus the suitable or applicable mechanism of cleaving the cleavable additive of formula I is preferably adapted to or selected according to the nature of the at least one surface of the semiconductor substrate to be modified or treated, preferably by adapting to or selecting the linking group L as part of the compound of formula I, to meet a required mechanism of cleaving the cleavable additive of formula I, as explained in more detail below.

According to the present invention, cleaving of said compound of formula I is preferably induced by the trigger of heat, preferably at a cleaving temperature in the range of from 100 to 400° C., more preferably in the range of from 125 to 300° C., most preferably in the range of from 150 to 250° C. As a skilled person in the field will understand, higher temperatures of the temperature ranges as defined before can be applied to semiconductor substrates, in particular semiconductor wafers or intermediate semiconductor wafers, at the start of their production, i.e. where the semiconductor substrate or wafer does not yet comprise a variety of coatings, patterns or structures of materials which may be sensitive to elevated temperatures, and that only lower temperatures of the temperature ranges as defined before can be applied to semiconductor substrates, in particular semiconductor wafers, at later stages of their production or towards the end of their production process. The cleaving temperatures applied are therefore preferably selected so that layers, coatings, patterns or structures on the semiconductor substrate to be modified and/or treated are not compromised, damaged or destroyed by the application of said temperatures.

This rationale for selecting a suitable temperature applies equally to selecting a suitable cleaving temperature and for selecting a suitable temperature for removal of the set of fragments of the compound of formula I from the at least one surface of the semiconductor substrate.

Unlike methods known from the prior art where e.g. cleavable surfactants were to be removed at temperatures suitable for or compatible with physiological processes, like at temperatures in the range of from 60° C. to (short-time exposure) 90° C. or 105° C. and usually at ambient pressure (see e.g. documents WO 2009/048611 or U.S. Pat. No. 7,022,861), the cleavable additives (compounds of formula I, preferably the compounds of formula Ib) for use in the present invention are preferably cleaved (decomposed) and/or evaporated at higher temperatures and/or reduced pressures (as explained above and below), i.e. under conditions which are compatible with or possible to be used in industrial processes for producing semiconductor substrates, preferably semiconductor wafers, and/or microelectronic devices.

In one variant of the above-defined use of the present invention, said removal of said compound of formula I from the at least one surface of said semiconductor substrate is done by rinsing or rinsing off said fragments or set of fragments from said surface. In this variant, the previous cleaving of said compound of formula I preferably reduces adhesion of the resulting fragments from said set of fragments to the at least one surface of a semiconductor substrate and thus facilitates removal of the compound of formula I (viz. its fragments) from said surface.

In a preferred variant of the above-defined use of the present invention, said removal of said compound of formula I from the at least one surface of said semiconductor substrate is done by evaporation of said set of fragments from said surface, particularly preferably where cleaving of said compound of formula I into a set of fragments is induced by the trigger of heat, as explained above. Evaporation of said set of fragments is preferably done by heating, preferably by heating to a temperature in the range of from 100 to 400° C. ("cleaving temperature"), more preferably in the range of from 125 to 300° C., most preferably in the range of from 150 to 250° C., or to a temperature below said cleaving temperature and/or at an evaporation pressure. Preferably, the evaporation pressure is a reduced pressure, preferably a pressure of not more than 10 hPa, more preferably of not more than $10^{-2}$ hPa and yet more preferably of not more than $10^{-3}$ hPa.

Evaporation is preferred in all aspects (use, method of making, method of cleaning and/or rinsing) of the present invention as method for removal of said set of fragments of the compound of formula I, as it is a versatile, convenient, quick and easy method which can be introduced at most or all processing steps in a method of making a semiconductor substrate or microelectronic device, or a method of cleaning or rinsing a semiconductor substrate (i.e. "at the point of use").

Particularly preferred are uses and methods of the invention as defined (or as defined as preferred) in this text where said cleaving of said compound of formula I is induced by the trigger of heat and removing said resulting set of fragments is done by evaporation.

If the removal of said compound of formula I from said surface is done by evaporation, preferably, the compound of formula I and/or the fragments into which it is being cleaved subsequent to said modification or treatment should not represent, form or decompose into non-volatile or low volatile compounds, fragments or pieces and/or should not cause any side reactions upon their decomposition or thermal removal which may be obstructive to removal or complete removal of the compound of formula I from said at least one surface of a semiconductor substrate. Preferably, the compound of formula I and their respective groups A and B are selected so as to comply with this requirement.

Preferred is also a use according to the invention (or a use according to the present invention which is designated as being preferred in this text), wherein
said semiconductor substrate is selected from the group consisting of
a semiconductor wafer,
an intermediate semiconductor wafer; and
a microelectronic device,
and/or
said modification or treatment of at least one surface of a semiconductor substrate is treatment and more preferably is cleaning and/or rinsing,
and/or
cleaving of said compound of formula I is induced by the trigger of heat, preferably at a cleaving temperature in the range of from 100 to 400° C., more preferably in the range of from 125 to 300° C. and most preferably in the range of from 150 to 250° C.,
and/or
said removal is done by evaporation, preferably at said cleaving temperature in the range of from 100 to 400° C., more preferably in the range of from 125 to 300° C., most preferably in the range of from 150 to 250° C.; or
at a temperature below said cleaving temperature.

In a preferred variant of the present invention, a use according to the invention (or a use according to the present invention which is designated as being preferred in this text) is preferred, wherein
in the compound of formula I or its salt,
L is selected from the group consisting of acetal groups; ketal groups; ester groups; thioester groups; ortho ester groups; carbonate groups; amide groups; organosilyl groups, Diels-Alder adducts, urethane groups, disulfide groups, diazosulfonate groups and alkylarylketone sulfonate groups;
and preferably L is a urethane group,
and/or (preferably and)
L is bonded via covalent bonds to any of A and B,
and/or (preferably and)
A and B are different
and preferably
A is selected from the group consisting of
a hydrophobic group, preferably a straight-chain or branched $C_4$-$C_{20}$-alkyl group, which is substituted by 1 to 4 ether groups or is preferably unsubstituted;
a solubilizing group;
a sterically hindering group;
a group improving packaging;
a repelling group and
a precursor group for forming self-assembled monolayers,
and preferably A is a hydrophobic group, more preferably a straight-chain or branched $C_4$-$C_{20}$-alkyl group, which is substituted by 1 to 4 ether groups or is preferably unsubstituted,
and/or (preferably and)
B is selected from the group consisting of
a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups;
- an adhesive group with affinity to the at least one surface of a microelectronic device;
- a water film binding group;
- an anchoring group reactive to the at least one surface of a microelectronic device;
- an anchoring group adsorbing to the at least one surface of a microelectronic device;
- an anchoring group reactive to Si—OH bonds and an alkyl-silyl group;
  and preferably B is a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups, and/or the compound of formula I or its salt has a molecular weight not exceeding 1500 g/mol, preferably not exceeding 1000 g/mol.

For the use or a preferred use according to the invention, the tail group A and the head group B as parts of the compound of formula I are preferably adapted or selected to meet a required purpose of modifying or treating at least one surface of a semiconductor substrate, preferably a semiconductor wafer:

If the purpose of the compound of formula I is cleaning or rinsing, the tail group A is preferably a hydrophobic group, more preferably straight-chain or branched $C_4$-$C_{20}$-alkyl, which is substituted by 1 to 4 ether groups or is preferably unsubstituted; and the head group B is preferably a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups If the purpose of the compound of formula I is rinsing with particular emphasis on avoiding the effects of pattern collapse (as explained above), the tail group A is preferably selected from the group consisting of a hydrophobic group, more preferably straight-chain or branched $C_4$-$C_{20}$-alkyl, which is substituted by 1 to 4 ether groups or is preferably unsubstituted; and a repelling group; and the head group B is preferably selected from the group consisting of a water film binding group, an anchoring group reactive to the at least one surface of a semiconductor substrate and an anchoring group adsorbing to the at least one surface of a semiconductor substrate.

If the purpose of the compound of formula I is pore-sealing of low-k dielectric materials (as explained above), the head group is preferably selected from the group consisting of a sterically hindering group and a precursor group for forming self-assembled monolayers; and the head group B is preferably selected from the group consisting of a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups; and an anchoring group adsorbing to the at least one surface of a semiconductor substrate.

If the purpose of the compound of formula I is repairing films of low-k dielectric materials (as explained above), the tail group A is preferably a solubilising group; and the head group B is preferably selected from the group consisting of an anchoring group reactive to Si—OH bonds and an alkyl-silyl group.

If the purpose of the compound of formula I is inhibiting corrosion (as explained above), the tail group A is preferably selected from the group consisting of a solubilising group, a sterically hindering group and a group improving packaging; and the head group B is preferably a group with affinity to the at least one surface of a semiconductor substrate.

For the use or a preferred use and other aspects of the invention, the linking group L as part of the compound of formula I is preferably adapted or selected to meet a required mechanism of cleaving the cleavable additive of formula I. The mechanism of cleaving the cleavable additive of formula I is preferably adapted to the nature of the at least one surface of the semiconductor substrate, preferably the semiconductor wafer, i.e. if said surface is patterned or unpatterned and/or if it e.g. carries layers of non-semiconducting materials which need to be preserved but may be sensitive to or incompatible with particular treatment methods. Accordingly, the linking group L is preferably selected from the group consisting of:

- heat- or thermally labile linking groups L, preferably a urethane group and/or Diels-Alder adducts, more preferably a urethane group. A heat- or thermally-labile group is selectively cleaved or rearranged by the trigger of heat, in the context of the present invention preferably at a cleaving temperature in the range of from 100 to 400° C., more preferably in the range of from 125 to 300° C., most preferably in the range of from 150 to 250° C.;
- acid-labile linking groups L, preferably acetal groups; ketal groups and/or ortho ester groups. An acid-labile linking group L is selectively cleaved or rearranged when induced by the trigger of pH change, preferably by the trigger of pH reduction and/or by the trigger of acid treatment;
- alkaline-labile linking groups L, preferably ester groups and/or thioester groups. An alkaline-labile linking group L is selectively cleaved or rearranged when induced by the trigger of pH change, preferably by the trigger of pH increase and/or by the trigger of alkaline (base) treatment;
- irradiation-labile linking groups L, preferably UV-irradiation-labile groups L, preferably alkylarylketone sulfonate groups; diazosulfonate groups and/or disulfide groups. An irradiation-labile linking group L is selectively cleaved or rearranged when induced by the trigger of electromagnetic irradiation, preferably by irradiation with UV light, more preferably with UV light of a wavelength in the range of from 190 to 400 nm;
- redox-labile linking groups L, preferably disulfide groups. A redox-labile group L is selectively cleaved or rearranged when induced by the trigger of chemical reduction or chemical oxidation;
- enzymatic-labile linking groups L, preferably ester groups, amide grous and/or carbonate groups. An enzymatic labile group is selectively cleaved or rearranged when induced by the trigger of enzymatic conversion. Enzymatic conversion is often substrate-specific;

nucleophil- or electrophil-labile groups L, preferably organosilyl groups. A nucleophilor electrophil-labile group L is selectively cleaved or rearranged when induced by the trigger of a nucleophil or electrophil attack, e.g. a nucleophil attack by a fluoride anion.

Linking groups L and suitable methods of selecting and/or selectively cleave or rearrange said linking groups L which are also suitable for use or application in the compound of formula I of the present invention are generally known in the field, e.g. from documents U.S. Pat. No. 7,022,861; WO 2009/048611 A2 or WO 02/097393 A2, or by A. Tehrani-Bagha et al., Current Opinion in Colloid & Interface Science, Vol. 12 Is. 2 (2007) 81-9, or literature cited therein. The disclosures of the foregoing documents are therefore incorporated herein by reference in their entireties For the purposes of the present invention in all its aspects (use, method of making, method of cleaning), heat- or thermally labile linking groups L are preferred as they do not require addition of any further reagents or chemicals (e.g. acids, bases or nucleophils) and therefore usually allow more universal applications, e.g. in different production environments and/or on surfaces of a microelectronic device of different natures (patterned, unpatterned, coated, uncoated.

In one preferred variant of the present invention, the compound of formula I therefore is a compound of formula Ia:

$$A\text{-}N(H)\text{—}C(O)O\text{—}B \qquad (Ia),$$

wherein A and B have the meanings as defined above (or as defined above as preferred) for the compound of formula I and are connected via a urethane group "—N(H)—C(O)O—".

In a further variant of the present invention, a use according to the invention (or a use according to the present invention which is designated as being preferred in this text) is preferred, wherein in the compound of formula I or its salt, A is a straight-chain or branched aliphatic hydrocarbon group having a total number of 4 to 20, preferably of 6 to 16, carbon atoms, which is substituted by 1 to 4 ether groups, or is preferably unsubstituted, and/or (preferably and)

B is a straight-chain or branched aliphatic hydrocarbon group having a total number of 1 to 6, preferably of 1 to 4, carbon atoms, which is substituted by one or two, preferably one, ionic groups, independently selected from anionic groups, preferably carboxylate, sulfate, sulfonate or phosphate, more preferably carboxylate; and cationic groups, preferably ammonium which is unsubstituted or substituted by 1 to 3 straight-chain or branched $C_1$-$C_4$-alkyl groups, preferably unsubstituted ammonium;

and/or (preferably and)

L is a urethane group (—N(H)—C(O)O—), and/or the cleavable additive is a cleavable surfactant;

and/or said semiconductor substrate is a semiconductor wafer.

In yet a further variant, a use according to the invention (or a use according to the present invention which is designated as being preferred in this text) is preferred, wherein cleaving of said compound of formula I is induced by the trigger of heat, preferably at a cleaving temperature in the range of from 100 to 400° C., more preferably in the range of from 125 to 300° C. and most preferably in the range of from 150 to 250° C., and/or said removal is done by evaporation, preferably at a temperature, more preferably at said cleaving temperature, in the range of from 100 to 400° C., more preferably in the range of from 125 to 300° C. and most preferably in the range of from 150 to 250° C.; or at a temperature below said temperature, preferably at a temperature below said cleaving temperature.

For the use or a preferred use and other aspects of the invention, the compound of formula I or its salt preferably has a molecular weight not exceeding 1500 g/mol, preferably not exceeding 1000 g/mol. A compound of formula I or its salt which has a molecular weight in the specified range can preferably be cleaved into a set of fragments where the fragments can be removed, preferably completely removed, from the surface of a semiconductor substrate by the preferred removal by evaporation (as explained in more detail below), under conditions compatible with the usual conditions and/or requirements when processing semiconductor substrates, preferably semiconductor wafers, like suitable processing temperatures (as defined above) and/or pressures (as defined below), preferably at said cleaving temperature in the range of from 100 to 400° C., more preferably in the range of from 125 to 300° C. and most preferably in the range of from 150 to 250° C.; or at a temperature below said cleaving temperature.

Similarly, where the tail group A is a is a straight-chain or branched aliphatic hydrocarbon group as defined above and the head group B is a polar, substituted straight-chain or branched aliphatic hydrocarbon group as defined above, the resulting fragments from thermally cleaving a respective compound of formula I are preferably fragments which can be removed by evaporation, preferably by evaporation at a temperature in the range of from 100 to 400° C., more preferably in the range of from 125 to 300° C. and most preferably in the range of from 150 to 250° C. and/or (preferably "or") at a pressure ("evaporation pressure") of not more than 10 hPa, preferably of not more than $10^{-2}$ hPa, more preferably of not more than $10^{-3}$ hPa.

For the use or a preferred use of the compound of formula I or its salt and other aspects of the invention, the linking group L is preferably a urethane group (—N(H)—C(O)O—). A compound of formula I or its salt, preferably a preferred compound of formula I or its salt, wherein the linking group L is a urethane group can preferably be cleaved into a set of fragments by the trigger of heat, preferably at a cleaving temperature in the range of from 100 to 400° C., more preferably in the range of from 125 to 300° C. and most preferably in the range of from 150 to 250° C. It has been shown in own experiments that said thermal cleavage of a urethane group L is usually proceeding smoothly at a temperature not exceeding 200° C.

It has been found in own experiments that compounds of formula I where the linking group L is a urethane group, preferably compounds of formula Ia, more preferably compounds of formula Ib (as defined below), are, induced by the trigger of heat, selectively cleaved into a set of fragments and are nearly completely, preferably completely removed from the surface of a semiconductor wafer induced by evaporation. In own experiments it could also be shown (see the examples section) that—under comparable conditions certain cleavable surfactants from the Diels-Alder adduct type could not be completely removed from the surface of a semiconductor wafer induced by evaporation but that significant amounts of residuals from organic compounds were found after heating and evaporation of said cleavable surfactants from the Diels-Alder adduct type.

A use or according to the invention (or a use according to the present invention which is designated as being preferred in this text) is also preferred, where
in the compound of formula I or its salt,
A is a straight-chain or branched aliphatic hydrocarbon group having a total number of 4 to 20, preferably of 6 to 16, carbon atoms, which is substituted by 1 to 4 ether groups or is preferably unsubstituted,
and
B is a straight-chain or branched aliphatic hydrocarbon group having a total number of 1 to 6, preferably of 1 to 4, carbon atoms, which is substituted by one or two, preferably one, ionic groups, independently selected from anionic groups, preferably carboxylate, and cationic groups, preferably ammonium which is substituted by 1 to 3 straight-chain or branched $C_1$-$C_4$-alkyl groups or is preferably unsubstituted;
and
L is a urethane group and is bonded via covalent bonds to any of A and B
and/or (preferably "and")
— the use of said compound of formula I or its salt is as cleavable surfactant,
and/or (preferably "and")
said use of said compound of formula I is as cleavable surfactant in the cleaning and/or rinsing of a semiconductor wafer.

In a further variant, a use according to the invention (or a use according to the present invention which is designated as being preferred in this text) is also preferred, wherein in the organic compound of formula I or its salt,
A is a monovalent group $R^1$—$CH_2$—, where
$R^1$ is a straight-chain or branched aliphatic hydrocarbon group having a total number of 4 to 20, preferably of 6 to 16, more preferably of 7 to 14, still more preferably of 7 to 12, carbon atoms;
B is a monovalent ionic group of formula II

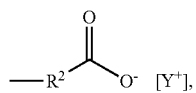

(II)

where
$R^2$ is a straight-chain or branched aliphatic hydrocarbon group having a total number of 1 to 6, preferably of 1 to 4, carbon atoms and
$Y^+$ is a singly charged ammonium cation which is unsubstituted or substituted by 1 to 3 straight-chain or branched $C_1$-$C_4$-alkyl groups; and preferably is unsubstituted ammonium,
and
L is a urethane group.

In this preferred variant, preferably said use of said compound of formula I is as cleavable surfactant in the cleaning and/or rinsing of at least one surface of a semiconductor wafer.

It has been found in own experiments that the compounds of formula I or the preferred compounds of formula I as further specified here above are particularly suitable as cleavable surfactants in the cleaning or rinsing of a semiconductor wafer as they can be cleaved into a set of fragments by the trigger of heat, preferably at a cleaving temperature in the range of from 100 to 400° C., more preferably in the range of from 125 to 300° C. and most preferably in the range of from 150 to 250° C. and said fragments, subsequently to said cleaning or rinsing, can be removed, preferably completely removed (as defined above), from the surface of said semiconductor substrate by the preferred removal induced by evaporation (as explained in more detail below), preferably at said cleaving temperature in the range of from 100 to 400° C., more preferably in the range of from 125 to 300° C. and most preferably in the range of from 150 to 250° C.; or at a temperature below said cleaving temperature and/or at a cleaving pressure, preferably an evaporation pressure (as defined above).

Preferred is the use according to the present invention of a compound of formula I as defined above (or a use according to the present invention which is designated as being preferred in this text), wherein said modification or treatment, preferably said cleaning or rinsing, is part of a process, preferably an industrial process, of making microelectronic devices, circuit devices, optical devices, electronic displays and/or mechanical precision devices, preferably microelectronic devices.

The present invention also relates to a method of making a semiconductor substrate, preferably a microelectronic device, comprising the following steps:
making or providing a semiconductor substrate, preferably a start semiconductor wafer or an intermediate semiconductor wafer, preferably an intermediate semiconductor wafer, having at least one surface,
contacting said at least one surface with an organic compound of formula (I):

A-L-B (I), or a salt thereof, wherein
A is a tail group,
B is a head group and
L is a linking group,
so that said surface is modified or treated,
and subsequently
cleaving said organic compound or its salt on said surface into a set of fragments,
and preferably, subsequently
removing, preferably completely removing, said set of fragments from the contacted surface,
and preferably subsequently
performing further subsequent steps
so that a semiconductor substrate, preferably a microelectronic device, results.

Generally, all aspects of the present invention discussed herein above in the context of the inventive use of an organic compound of formula I apply mutatis *mutandis* to the method of making of the present invention. And likewise all aspects of the method of making a semiconductor substrate according to the present invention discussed herein apply mutatis *mutandis* to the use according to the present invention of an organic compound of formula I.

The method of making as defined above preferably is a part of or is an industrial serial production, preferably in the interconnect industry, of a microelectronic device for application in electronic products, preferably including integrated circuits or devices comprising integrated circuits.

In the method of making as defined above, the step of contacting preferably comprises contacting said at least one surface of a start semiconductor wafer or an intermediate semiconductor wafer, preferably of an intermediate semiconductor wafer, with a compound of formula I, so that said surface is modified by at least one modification selected from the group consisting of pore-sealing of low-k dielectric materials, repairing films of low-k dielectric materials, changing the zeta-potential of at least one surface of the intermediate semiconductor substrate, changing the contact angle on at least one surface of the intermediate semiconductor substrate, changing the adsorption or adhesion properties of at least one surface of the intermediate semiconductor substrate in relation to the compound of formula I and inhibiting corrosion and/or so that said surface is treated by at least one treatment selected from the group consisting of cleaning and rinsing. Preferably, the step of contacting comprises contacting said at least one surface so that said surface is cleaned or rinsed.

Preferred is also a method of making according to the present invention as defined above wherein
  said step of contacting is conducted so as to achieve at least one effect selected from the group consisting of modifying, preferably by pore-sealing of low-k dielectric materials, repairing films of low-k dielectric materials, changing the zeta-potential of at least one surface of the intermediate semiconductor substrate, changing the contact angle on at least one surface of the intermediate semiconductor substrate, changing the adsorption or adhesion properties of at least one surface of the intermediate semiconductor substrate in relation to the compound of formula I and/or inhibiting corrosion; and treating, preferably by cleaning and rinsing;
    wherein preferably the at least one effect is or comprises cleaning and/or rinsing, more preferably comprising defect reduction rinses, post-ash residue removal rinses, post-etch residue removal rinses and photoresist residue removal rinses,
  and/or
  said step of cleaving comprises thermally cleaving said compound of formula I or its salt into a set of fragments,
    preferably at a cleaving temperature in the range of from 100 to 400° C., more preferably in the range of from 125 to 300° C., most preferably in the range of from 150 to 250° C.; and/or at a cleaving pressure,
  and/or
  said step of removing said set of fragments from the at least one contacted surface comprises evaporating fragments, preferably
    at said cleaving temperature in the range of from 100 to 400° C., more preferably in the range of from 125 to 300° C., most preferably in the range of from 150 to 250° C.; or at a temperature below said cleaving temperature
    and/or
    at said cleaving pressure or at a pressure below said cleaving pressure.

In the preferred method of making as defined above, said step of thermally cleaving said compound of formula I is preferably induced by the trigger of heat.

In the preferred method of making as defined above, said cleaving pressure is preferably ambient pressure (atmospheric pressure) and said pressure below said cleaving pressure is preferably a reduced pressure, preferably a pressure of not more than 10 hPa, more preferably of not more than $10^{-2}$ hPa and yet more preferably of not more than $10^{-3}$ hPa ("evaporation pressure").

In the context of the present invention, "removing" the set of fragments of the compound of formula I from the contacted surface preferably means that at least 99.5 mass-% of the compound of formula I (viz. its fragments) is removed from said contacted surface as a result of the method of making according to the present invention, preferably as determined by differential measurement of masses. I.e. not more than 0.5 mass-% of the total mass of the compound of formula I previously applied in the step of contacting said at least one surface with the organic compound of formula (I) is found after the steps of cleaving and removing of the method of making according to the present invention (as defined above) have been conducted.

In the context of the present invention, "completely removing" the set of fragments of the compound of formula I from the contacted surface preferably means that at least 99.9 mass-% of the compound of formula I (viz. its fragments) are removed from said contacted surface as a result of the method of making according to the present invention, preferably as determined by differential measurement of masses. I.e. not more than 0.1 mass-% of the total mass of the compound of formula I previously applied in the step of contacting said at least one surface with the organic compound of formula (I) is found after the steps of cleaving and removing of the method of making according to the present invention (as defined above) have been conducted.

In cases where a direct test for successful "removing" or "completely removing" the compound of formula I or its fragments from the contacted surface of a semiconductor wafer according to the method of making of the present invention is not preferred, or in cases of doubt, an indirect measuring method is preferably used for determining if a certain compound of formula I or Ia, which can be cleaved by the trigger of heat, preferably a compound of formula Ib, is or can be "removed" or "completely removed" by the method of making according to the present invention (as defined above), i.e. under the conditions of the method of making according to the present invention.

A method of making according to the invention (or a method of making according to the present invention which is designated as being preferred in this text) is therefore also preferred, wherein
  the compound of formula I is a compound of formula Ib
  and/or
  the step of removing comprises removing at least 99.1 mass-%, preferably at least 99.9 mass-%, of the compound of formula I, preferably of the compound of formula Ib, from the contacted surface by removing said set of its fragments, preferably as determined by differential measurement of masses,
  whereby preferably said removing of at least 99.1 mass-%, preferably of at least 99.9 mass-%, of the compound of formula I or Ib is (indirectly) determined by a test method comprising the steps:
    loading a defined mass of a compound of formula I or Ib into a quartz glass tube, preferably a cylindrical quartz glass tube with a length of 3 cm and a diameter of 20 cm,
    applying to the compound of formula I or Ib in the quartz glass tube for a period of 30 min the following treatment conditions:
      a pressure in the range of from atmospheric pressure to $10^{-3}$ hPa and
      a temperature in the range of from 100° C. to 400° C., preferably in the range of from 150° C. to 250° C.

Determining the degree of removal of a compound of formula I, preferably of formula Ib by differential measurement of masses is preferably conducted in the context of the present invention according or analogous to the method described in example 3, below.

In a further variant, a method of making according to the invention as defined above (or a method of making according to the present invention which is designated as being preferred in this text) is preferred, wherein
in the compound of formula I or its salt,
A and B are different and L is bonded via covalent bonds to A and B,
and/or (preferably and)
A is a straight-chain or branched aliphatic hydrocarbon group having a total number of 4 to 20, preferably of 6 to 16, carbon atoms, which is substituted by 1 to 4 ether groups or is preferably unsubstituted,
and/or (preferably and)
B is a straight-chain or branched aliphatic hydrocarbon group having a total number of 1 to 6, preferably of 1 to 4, carbon atoms, which is substituted by one or two, preferably one, ionic groups, independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups,
and/or (preferably and)
L is a urethane group,
and/or
the compound of formula I or its salt has a molecular weight not exceeding 1500 g/mol, preferably not exceeding 1000 g/mol.

In a variant of the method of making according to the invention as defined above (or a method of making according to the present invention which is designated as being preferred in this text) a method is preferred wherein the step of contacting said at least one surface with a compound of formula I or a salt thereof comprises contacting said at least one surface with a composition, preferably an aqueous composition (i.e. a composition containing water), comprising the compound of formula I or the salt thereof.

In a specific variant of the method of making of the present invention as defined above (or a method of making according to the present invention which is designated as being preferred in this text), the invention also relates to a method of cleaning and/or rinsing a semiconductor substrate, preferably an intermediate semiconductor wafer, comprising the following steps:
making or providing a semiconductor substrate, preferably an intermediate semiconductor wafer, having at least one surface and having one or more materials on at least one of its surfaces,
contacting said one or more materials on at least one surface of the semiconductor substrate, preferably the intermediate semiconductor wafer, with an organic compound, preferably a cleavable surfactant, of formula I:

$$A\text{-}L\text{-}B \qquad (I),$$

or a salt thereof, wherein
A is a tail group,
B is a head group and
L is a linking group,
removing an amount of said compound, preferably cleavable surfactant, of formula I or its salt from said at least one surface, together with one or more of said materials, so that a cleaned or rinsed semiconductor substrate, preferably intermediate semiconductor wafer, results, having attached to one or more of its surfaces a residual amount of said compound of formula I or its salt,
cleaving at least a fraction of or the total of said residual amount of said compound, preferably cleavable surfactant, of formula I or its salt on said surface(s) into a set of fragments by heating to a cleaving temperature at a cleaving pressure, each fragment having a boiling point below said cleaving temperature, at the cleaving pressure, preferably at the evaporation pressure, applied, and
removing, preferably completely removing, said set of fragments from the contacted surface by evaporation, preferably so that a cleaned or rinsed semiconductor substrate, preferably intermediate semiconductor wafer, results.

Generally, all aspects of the present invention discussed herein above in the context of the inventive use of an organic compound of formula I and the inventive method of making a semiconductor substrate apply mutatis *mutandis* to the method of cleaning or rinsing a semiconductor substrate of the present invention. And likewise all aspects of the inventive method of cleaning or rinsing a semiconductor substrate discussed herein apply mutatis *mutandis* to the use according to the present invention of an organic compound of formula I and/or the inventive method of making a semiconductor substrate.

In the method of cleaning or rinsing according to the invention as defined above, preferably said materials are residuals, residues, particles, working fluids and/or working liquids originating from previous processing steps. Preferably such materials are not tightly bonded, linked or fixed to the surface of said microelectronic device or intermediate microelectronic device but are seated on said surface loosely enough to be washed or rinsed off, preferably in cleaning (washing, rinsing) processes conventional in the industry. In particular, said materials may be particles, pieces or fragments which may have formed as a result of previous processing steps of e.g. post-etch residuals and/or residuals from photoresist layers or other layers which may have previously been applied to the surface of said semiconductor substrate or intermediate semiconductor substrate; and/or said materials may be working fluids or working liquids which may be present from previous processing steps and/or from preparing the semiconductor substrate or intermediate semiconductor substrate for drying after a rinsing step.

In the method of cleaning or rinsing according to the invention as defined above, in the step of cleaving at least a fraction of or the total of said residual amount of said organic compound, cleaving 99.5 mass-% or the total of said residual amount of said organic compoundis preferred.

In the method of cleaning or rinsing according to the invention as defined above, preferably each fragment resulting from cleaving said compound of formula I has a boiling point which is lower than the un-decomposed compound of formula I so that removing, preferably evaporating, the fragments resulting from cleaving said compound of formula can be achieved with less effort (i.e. at lower temperatures and/or at higher evaporation pressure), compared to the un-decomposed compound of formula I (as also explained above).

Furthermore, a method of cleaning and/or rinsing according to the present invention as defined above is preferred, wherein the step of removing said set of fragments comprises evaporating said fragments
at said cleaving temperature, preferably in the range of from 100 to 400° C., more preferably in the range of from 125 to 300° C., most preferably in the range of from 150 to 250° C.; or at a temperature below said cleaving temperature
and/or (preferably and)

at said cleaving pressure or at a pressure below said cleaving pressure, preferably at a pressure below said cleaving pressure, more preferably at a pressure of not more than $10^{-2}$ hPa, yet more preferably of not more than $10^{-3}$ hPa.

In one variant of the present invention, a method of cleaning and/or rinsing according to the present invention as defined above (or a method of cleaning and/or rinsing according to the present invention which is designated as being preferred in this text) is preferred, wherein in said compound of formula I or its salt, A is a monovalent group $R^1$—$CH_2$—, where
$R^1$ is a straight-chain or branched aliphatic hydrocarbon group having a total number of 4 to 20, preferably of 6 to 16, carbon atoms;

B is a monovalent ionic group of formula II

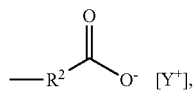

(II)

where
$R^2$ is a straight-chain or branched aliphatic hydrocarbon group having a total number of 1 to 6, preferably of 1 to 4, carbon atoms and
$Y^+$ is a singly charged ammonium cation which is unsubstituted or substituted by 1 to 3 straight-chain or branched $C_1$-$C_4$-alkyl groups; and preferably is unsubstituted ammonium,
and
L is a urethane group.

In a further variant of the present invention, a method of cleaning and/or rinsing according to the present invention as defined above (or a method of cleaning and/or rinsing according to the present invention which is designated as being preferred in this text) is preferred, wherein the step of contacting said at least one surface with a compound, preferably a cleavable surfactant, of formula I or a salt thereof comprises contacting said at least one surface with a composition, preferably an aqueous composition (i.e. a composition containing water), comprising the compound, preferably the cleavable surfactant, of formula I or the salt thereof.

The invention also relates to a compound of formula Ib,

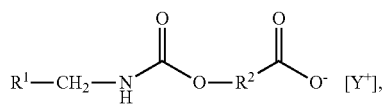

(Ib)

wherein
$R^1$ is a straight-chain or branched aliphatic hydrocarbon group having a total number of 4 to 20, preferably of 6 to 16, carbon atoms,
$R^2$ is a straight-chain or branched aliphatic hydrocarbon group having a total number of 1 to 6, preferably of 1 to 4, carbon atoms,
wherein preferably $R^2$ does not comprise a chiral center
and
$Y^+$ is a singly charged ammonium cation which is unsubstituted or substituted by 1 to 3 straight-chain or branched $C_1$-$C_4$-alkyl groups; and preferably is unsubstituted ammonium,
and
wherein preferably
$R^1$ is a straight-chain or branched aliphatic hydrocarbon group having a total number of 7 to 14, more preferably of 7 to 12 carbon atoms,
and yet more preferably, $R^1$, together with the methylen group (i.e. the "—$CH_2$—" group) to which it is bonded, is an aliphatic hydrocarbon group selected from the group consisting of 2-ethylhexyl; 2-propylheptyl; n-dodecyl; 2,5,7,7-tetramethyloctyl; isodecyl; isotridecyl and a mixture of isotridecyl and isopentadecyl,
and most preferably $R^1$, together with the methylen group (i.e. the "—$CH_2$—" group) to which it is bonded, is an aliphatic hydrocarbon group selected from the group consisting of 2-propylheptyl; n-dodecyl and isotridecyl,
$R^2$ is a straight-chain or branched aliphatic hydrocarbon group having a total number of 1 to 2 carbon atoms and more preferably does not comprise a chiral center,
and yet more preferably $R^2$ is —$CH_2$—,
and
$Y^+$ is ammonium.

Generally, all aspects of the present invention discussed herein above in the context of the inventive use of an organic compound of formula I, the inventive method of making a semiconductor substrate and the inventive method of cleaning and/or rinsing a semiconductor substrate apply mutatis *mutandis* to the compound of formula Ib of the invention. And likewise all aspects of the compound of formula Ib of the invention discussed herein apply mutatis *mutandis* to the use of an organic compound of formula I, the inventive method of making a semiconductor substrate and the inventive method of cleaning and/or rinsing a semiconductor substrate.

The compound of formula Ib is particularly suitable and intended for application in the uses and methods of the invention, preferably in the use as cleavable additive, more preferably as cleavable surfactant, in the modification and/or treatment of at least one surface of a semiconductor substrate; in the method of making a semiconductor substrate, preferably a microelectronic device and/or in the method of cleaning and/or rinsing a semiconductor substrate, all as defined above in each case (or as defined above as preferred in each case).

In a preferred variant, the compound of formula Ib is a preferred compound of formula I in the use or a preferred use according to the invention as cleavable surfactant in the cleaning or rinsing of at least one surface of a semiconductor substrate, preferably comprising post-ash residue removal rinses, post-etch residue removal rinses and photoresist residue removal rinses.

In the compound of formula Ib according to the invention as defined above, $R^2$ preferably does not comprise a chiral center. Preferably, $R^2$ therefore preferably does not carry two different (geminal) substituents at the same carbon atom. More preferably, $R^2$ is selected from "—$CH_2$—" and "n-$C_2H_4$—" and most preferably $R^2$ is "—$CH_2$—" (methylen).

In the compound of formula Ib as defined above, a preferred meaning of $R^1$, together with the methylen group to which it is bonded, is an "isodecyl" hydrocarbon group. "Isodecyl" denotes a mixture of isomers of a hydrocarbon group which has ten carbon atoms and an average branching degree in the range of from 2 to 2.5 (i.e. the $C_{10}$-isomers on average have 2 to 2.5 branches in their carbon chain). The branching degree can be determined by $^1$H-NMR spectroscopy as the amount of "$CH_3$—"groups (signals) minus one "$CH_3$—" group. The isodecyl group can be introduced into an organic molecule from commercially available sources, e.g. from isodecyl alcohol (CAS RN 25339-17-7). "Isodecyl" is abbreviated to "$iC_{10}H_{21}$" in the compound of formula VIII below.

In the compound of formula Ib as defined above, another preferred meaning of $R^1$, together with the methylen group to which it is bonded, is an "isotridecyl" hydrocarbon group. "Isotridecyl" denotes a mixture of isomers of a hydrocarbon group which has thirteen carbon atoms and an average branching degree in the range of from 2 to 3.5 (i.e. the $C_{13}$-isomers on average have 2 to 3.5 branches in their carbon chain). The isotridecyl group can be introduced into an organic molecule from commercially available sources, e.g. from isotridecyl alcohol (CAS RN 27458-92-0). "Isotridecyl" is abbreviated to "$iC_{13}H_{27}$" in the compound of formula V below.

In the compound of formula Ib as defined above, yet another preferred meaning of $R^1$, together with the methylen group to which it is bonded, is a mixture of "isotridecyl" and "isopentadecyl" hydrocarbon groups. Said mixture of ""isotridecyl" and "isopentadecyl" groups denotes a mixture of isomers of hydrocarbon group which has thirteen or fifteen carbon atoms, respectively, and an average branching degree in the range of from 0.1 to 0.9 (i.e. the $C_{13}$— or $C_{15}$-isomers on average have 0.1 to 0.9 branches in their carbon chain). The mixture of isotridecyl and isopentadecyl groups can be introduced into an organic molecule from commercially available sources, e.g. by a known hydroformylation reaction of corresponding commercially available alpha-olefins. The mixture of "isotridecyl" and "isopentadecyl" is abbreviated to "$iC_{13}H_{27}/iC_{15}H_{31}$" in the compound of formula IX below.

Particularly preferred compounds of formula Ib according to and for the uses and methods of the invention are selected from the group of compounds of formulas III to IX, shown below:

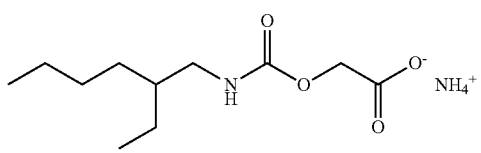

(III)

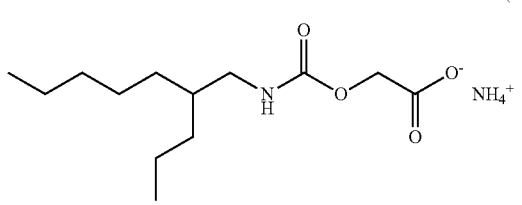

(IV)

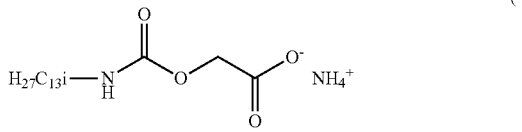

(V)

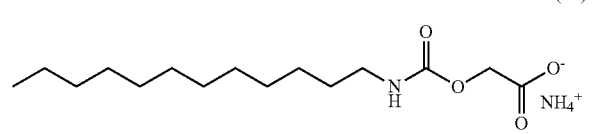

(VI)

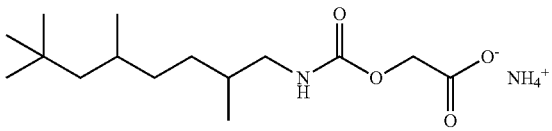

(VII)

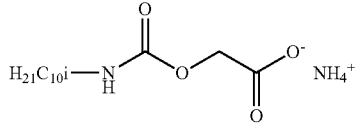

(VIII)

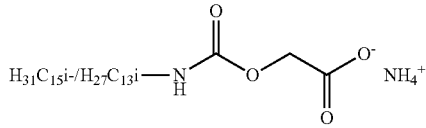

(IX)

Most preferred compounds of formula Ib for the uses and methods of the invention are the compounds of formulae III, IV and V, as shown above.

The invention also relates to a composition, comprising a compound of formula Ib or a salt thereof, and conventional solvents (including water) and/or additives.

The invention also relates to a use of a composition comprising a compound of formula I or a salt thereof, preferably as defined above (or as defined above as preferred) and/or a compound of formula Ib or a salt thereof, as defined above (or as defined above as preferred), for modifying or treating at least one surface of a semiconductor substrate.

Generally, all aspects of the present invention discussed herein above in the context of the inventive use of a compound of formula I, the inventive method of making a semiconductor substrate, preferably a microelectronic device, the inventive method of cleaning or rinsing a semiconductor substrate and/or the compounds of formula Ib according to the invention apply mutatis mutandis to the use of a composition comprising a compound of formula I or a salt thereof and/or a compound of formula Ib or a salt thereof. And likewise, all aspects of the inventive use of a composition comprising a compound of formula I or a salt thereof and/or a compound of formula Ib or a salt thereof discussed herein apply mutatis mutandis to the inventive use of a compound of formula I, the inventive method of making a semiconductor substrate, preferably a microelectronic device, the inventive method of cleaning or rinsing a semiconductor substrate and/or the compounds of formula Ib according to the invention The compounds of formula I as disclosed herein can be prepared by methods generally known in the art, e.g. by methods as disclosed in documents U.S. Pat. No. 7,022,861; WO 2009/048611 A2 or WO 02/097393 A2, or by A. Tehrani-Bagha et al., Current Opinion in Colloid & Interface Science, Vol. 12 Is. 2 (2007) 81-9, or literature cited therein, incorporated herein by reference (see above).

The compounds of formula Ib can preferably be prepared by the general procedure(s) provided in the examples section below.

The invention is further described and summarized in the following aspects A1 to A15:

A1. Use of an organic compound of formula I $$A-L-B \qquad (I),$$

or a salt thereof, wherein
A is a tail group,
B is a head group and
L is a linking group,
as cleavable additive in the modification and/or treatment of at least one surface of a semiconductor substrate,
where the compound of formula I is cleaved into a set of fragments subsequent to said modification or treatment, for facilitating its removal from said surface.

A2. Use according to aspect 1, wherein
in the compound of formula I or its salt,
L is selected from the group consisting of acetal groups; ketal groups; ester groups; thioester groups; ortho ester groups; carbonate groups; amide groups; organosilyl groups, Diels-Alder adducts, urethane groups, disulfide groups, diazosulfonate groups and alkylarylketone sulfonate groups;
and/or
L is bonded via covalent bonds to any of A and B,
and/or
A and B are different
and preferably
A is selected from the group consisting of
a hydrophobic group, preferably $C_4$-$C_{20}$-alkyl, which is substituted by 1 to 4 ether groups or is unsubstituted;
a solubilizing group;
a sterically hindering group;
a group improving packaging;
a repelling group and
a precursor group for forming self-assembled monolayers,
and preferably A is a hydrophobic group, more preferably $C_4$-$C_{20}$-alkyl, which is substituted by 1 to 4 ether groups or is unsubstituted, and/or
B is selected from the group consisting of
a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups;
an adhesive group with affinity to the at least one surface of a microelectronic device;
a water film binding group;
an anchoring group reactive to the at least one surface of a microelectronic device;
an anchoring group adsorbing to the at least one surface of a microelectronic device;
an anchoring group reactive to Si—OH bonds and
an alkyl-silyl group;
and preferably B is a polar group, preferably comprising in its chemical structure at least one ionic group independently selected from anionic groups, preferably carboxylate, sulfate, sulfonate or phosphate, and cationic groups, preferably ammonium which is unsubstituted or substituted by 1 to 3 straight-chain or branched $C_1$-$C_4$-alkyl groups,
and/or
the compound of formula I or its salt has a molecular weight not exceeding 1500 g/mol, preferably not exceeding 1000 g/mol.

A3. Use according to any of the preceding aspects, wherein in the compound of formula I or its salt,
A is a straight-chain or branched aliphatic hydrocarbon group having a total number of 4 to 20, preferably of 6 to 16, carbon atoms, which is substituted by 1 to 4 ether groups, or is unsubstituted,
and/or
B is a straight-chain or branched aliphatic hydrocarbon group having a total number of 1 to 6, preferably of 1 to 4, carbon atoms, which is substituted by one or two ionic groups independently selected from anionic groups, preferably carboxylate, sulfate, sulfonate or phosphate; and cationic groups, preferably ammonium which is unsubstituted or substituted by 1 to 3 straight-chain or branched $C_1$-$C_4$-alkyl groups;
and/or
L is a urethane group.
and/or
the cleavable additive is a cleavable surfactant.

A4. Use according to any of the preceding aspects, preferably according to aspect 3, wherein
cleaving of said compound of formula I is induced by the trigger of heat, preferably at a cleaving temperature in the range of from 100 to 400° C., more preferably in the range of from 125 to 300° C. and most preferably in the range of from 150 to 250° C.,
and/or
said removal is done by evaporation, preferably at a temperature in the range of from 100 to 400° C., more preferably in the range of from 125 to 300° C., most preferably in the range of from 150 to 250° C.; or at a temperature below said temperature.

A5. Use according to any of the preceding aspects, wherein
said semiconductor substrate is selected from the group consisting of a semiconductor wafer, an intermediate semiconductor wafer and a microelectronic device,
and/or
said modification is selected from the group consisting of pore-sealing of low-k dielectric materials, repairing films of low-k dielectric materials, changing the zeta-potential of at least one surface of the semiconductor substrate, changing the contact angle on at least one surface of the semiconductor substrate, changing the adsorption or adhesion properties of at least one surface of the semiconductor substrate in relation to the compound of formula I and inhibiting corrosion;
and/or
said treatment is selected from the group consisting of cleaning and rinsing.

A6. Use according to any of the preceding aspects, preferably according to aspect 3, wherein in the compound of formula I or its salt,
A is a monovalent group $R^1$—$CH_2$—, where
$R^1$ is a straight-chain or branched aliphatic hydrocarbon group having a total number of 4 to 20, preferably of 6 to 16, carbon atoms;
B is a monovalent ionic group of formula II

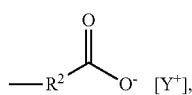

(II)

where
- $R^2$ is a straight-chain or branched aliphatic hydrocarbon group having a total number of 1 to 6, preferably of 1 to 4, carbon atoms and
- $Y^+$ is a singly charged ammonium cation which is unsubstituted or substituted by 1 to 3 straight-chain or branched $C_1$-$C_4$-alkyl groups; and preferably is unsubstituted ammonium, and L is a urethane group.

A7. Method of making a semiconductor substrate, comprising the following steps:
  making or providing a semiconductor substrate, preferably a start semiconductor wafer or an intermediate semiconductor wafer, having at least one surface,
  contacting said at least one surface with an organic compound of formula (I):

$$A\text{-}L\text{-}B \qquad (I),$$

or a salt thereof, wherein
  A is a tail group,
  B is a head group and
  L is a linking group,
  so that said surface is modified or treated,
  and subsequently
    cleaving said organic compound or its salt on said surface into a set of fragments
  and preferably subsequently
    removing said set of fragments from the contacted surface.

A8. Method according to aspect 7, wherein
  said step of contacting is conducted so as to achieve at least one effect selected from the group consisting of modifying by pore-sealing of low-k dielectric materials, repairing films of low-k dielectric materials, changing the zeta-potential of at least one surface of the intermediate semiconductor substrate, changing the contact angle on at least one surface of the intermediate semiconductor substrate, changing the adsorption or adhesion properties of at least one surface of the intermediate semiconductor substrate in relation to the compound of formula I and/or inhibiting corrosion; and treating by cleaning and/or rinsing;
    wherein preferably the at least one effect is or comprises cleaning and/or rinsing, more preferably comprising defect reduction rinses, post-ash residue removal rinses, post-etch residue removal rinses and photoresist residue removal rinses,
  and/or
  said step of cleaving comprises thermally cleaving said compound of formula I or its salt on said surface into a set of fragments,
    preferably at a cleaving temperature in the range of from 100 to 400° C., more preferably in the range of from 125 to 300° C., most preferably in the range of from 150 to 250° C. and at a cleaving pressure;
  and/or
  said step of removing said set of fragments from the at least one contacted surface comprises evaporating fragments, preferably
    at said cleaving temperature in the range of from 100 to 400° C., more preferably in the range of from 125 to 300° C., most preferably in the range of from 150 to 250° C.; or at a temperature below said cleaving temperature
    and/or
    at said cleaving pressure or at a pressure below said cleaving pressure.

A9. Method according to any of aspects 7 to 8, wherein in the compound of formula I or its salt,
  A and B are different and L is bonded via covalent bonds to A and B,
  and/or
  A is a straight chain or branched aliphatic hydrocarbon group having a total number of 4 to 20, preferably of 6 to 16, carbon atoms, which is substituted by 1 to 4 ether groups or is preferably unsubstituted,
  and/or
  B is a straight-chain or branched aliphatic hydrocarbon group having a total number of 1 to 6, preferably of 1 to 4, carbon atoms, which is substituted by one or two ionic groups, independently selected from anionic groups, preferably carboxylate, sulfate, sulfonate or phosphate, and cationic groups, preferably ammonium which is unsubstituted or substituted one to three times by $C_1$-$C_4$-alkyl,
  and/or
  L is a urethane group,
  and/or
  the compound of formula I or its salt has a molecular weight not exceeding 1500 g/mol, preferably not exceeding 1000 g/mol.

A10. Method, preferably according to any of aspects 7 to 9, of cleaning and/or rinsing a semiconductor substrate comprising the following steps:
  making or providing a semiconductor substrate having at least one surface and having one or more materials on at least one of its surfaces,
  contacting said one or more materials on at least one surface of the semiconductor substrate with an organic compound of formula I:

$$A\text{-}L\text{-}B \qquad (I),$$

or a salt thereof, wherein
  A is a tail group,
  B is a head group and
  L is a linking group,
  removing an amount of said compound of formula I or its salt from the at least one surface, together with one or more of said materials, so that a cleaned or rinsed semiconductor substrate results, having attached to one or more of its surfaces a residual amount of said compound of formula I or its salt,
  cleaving at least a fraction of or the total of said residual amount of said compound of formula I or its salt on said surface(s) into a set of fragments by heating to a cleaving temperature at a cleaving pressure, each fragment having a boiling point below said cleaving temperature, at the cleaving pressure applied, and
  removing, preferably completely removing said set of fragments from the contacted surface by evaporation.

A11. Method according to aspect 10, wherein the step of removing said set of fragments comprises evaporating said fragments
  at said cleaving temperature, preferably in the range of from 100 to 400° C., more preferably in the range of from 125 to 300° C., most preferably in the range of from 150 to 250° C.; or at a temperature below said cleaving temperature
  and/or
  at said cleaving pressure or at a pressure below said cleaving pressure.

A12. Method according to any of aspects 10 to 11, wherein in said compound of formula I or its salt,
A is a monovalent group R¹—CH₂—, where
R¹ is a straight-chain or branched aliphatic hydrocarbon group having a total number of 4 to 20, preferably of 6 to 16, carbon atoms;
B is a monovalent ionic group of formula II

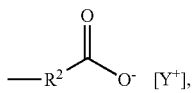
(II)

where
R² is a straight-chain or branched aliphatic hydrocarbon group having a total number of 1 to 6, preferably of 1 to 4, carbon atoms and
Y⁺ is a singly charged ammonium cation which is unsubstituted or substituted by 1 to 3 C₁-C₄-alkyl groups; and preferably is unsubstituted ammonium, and
L is a urethane group.

A13. Compound of formula Ib,

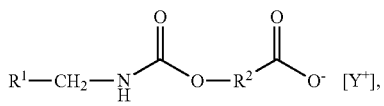
(Ib)

wherein
R¹ is a straight-chain or branched aliphatic hydrocarbon group having a total number of 4 to 20, preferably of 6 to 16, carbon atoms,
R² is a straight-chain or branched aliphatic hydrocarbon group having a total number of 1 to 6, preferably of 1 to 4, carbon atoms,
wherein preferably R² does not comprise a chiral center
and
Y⁺ is a singly charged ammonium cation which is unsubstituted or substituted by 1 to 3 C₁-C₄-alkyl groups; and preferably is unsubstituted ammonium.

A14. Compound of formula Ib according to aspect 13, wherein
R¹ is a straight-chain or branched aliphatic hydrocarbon group having a total number of 7 to 14, more preferably of 7 to 12 carbon atoms,
and more preferably R¹, together with the methylen group to which it is bonded, is an aliphatic hydrocarbon group selected from the group consisting of 2-ethylhexyl; 2-propylheptyl; n-dodecyl; 2,5,7,7-tetrannethyloctyl; isodecyl; isotridecyl and isopentadecyl,
R² is a straight-chain or branched aliphatic hydrocarbon group having a total number of 1 to 2 carbon atoms and preferably does not comprise a chiral center,
and more preferably is —CH₂—,
and
Y⁺ is ammonium.

A15. Use of a composition comprising a compound of formula I or a salt thereof, as defined in any of aspects 1 to 6, and/or a compound of formula Ib or a salt thereof, as defined in any of aspects 13 to 14, for modifying or treating at least one surface of a semiconductor substrate.

EXAMPLES

The following examples are meant to further explain and illustrate the invention without limiting its scope.

Example 1: Synthesis of Compounds of Formula Ib

General Procedure:

a) Synthesis of Alkyl Isocyanates

Where a required isocyanate was not purchased (or was not commercially available), it was synthesized from the corresponding primary amine by treatment with diphosgene (CAS RN 503-38-8) according to the following general procedure (see reaction scheme 1, RS-1, below), as generally known in the art:

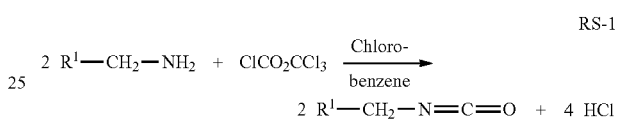
RS-1

R¹ and R² in reaction schemes 1 and 2 (RS-1, RS-2) have the meanings or preferred meanings as given above for the compound of formula Ib.

In a 1000 ml 4-necked round-bottom flask equipped with stirrer, thermometer and reflux condenser, the respective primary alkyl amine (1.0 molar equivalent) was dissolved in chloro benzene (2 g chloro benzene per 1 g alkyl amine) and stirred at room temperature for 20 min. After cooling to 0° C., diphosgene (1.0 molar equivalent) was added dropwise. The resulting mixture was stirred for 3 h at 0° C. and subsequently for 20 h at 20° C. Then the mixture was gently heated to 125° C. and stirred at this temperature for 8 h. The solvent was removed in a rotary evaporator at 80° C. and 10-20 hPa within 2 hours. The desired structure was confirmed by ¹H-NMR in each case. Where needed, the resulting isocyanate was purified by distillation.

b) Synthesis of Alkyl Urethane Alkylene Carboxylic Acid Methyl Esters

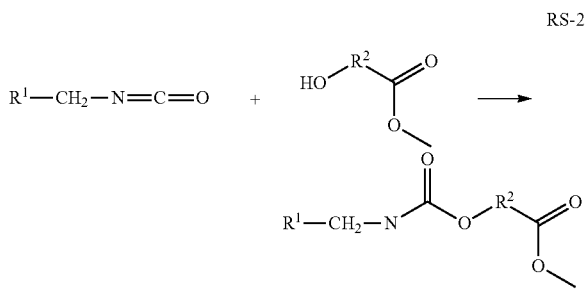
RS-2

In a 500 ml 4-necked round-bottom flask equipped with stirrer, thermometer and reflux condenser, the respective alkyl isocyanate (for preparation see procedural step a) above; 1.0 molar equivalent) was dissolved in dichloro methane (7.2 g dichloro methane per 1 g alkyl isocyanate)

and stirred at room temperature for 20 min. After cooling to 0° C., trimethylamine (0.1 molar equivalent) and N,N-dimethylaminopyridine (0.01 molar equivalent) was added. Then, glycolic acid methyl ester (1.0 molar equivalent) was added dropwise within 1 h at 0° C. The resulting mixture was allowed to warm to 20° C. and stirred for 20 h at this temperature. Then, the mixture was gently heated to 50° C. and stirred at this temperature for 20 h. The mixture was allowed to cool to 20° C. and a further amount of dichloro methane (6 g dichloro methane per 1 g alkyl isocyanate) was added. The organic phase was extracted with 1 M aqueous hydrochloric acid (half the volume of the dichloro methane volume). The organic layer was separated and dried over $MgSO_4$. The dried organic solvent was removed in a rotary evaporator at 40° C. and a pressure of 10-20 hPa within 4 hours. The desired structure was confirmed by $^1$H-NMR in each case.

c) Synthesis of Alkyl Urethane Alkylene Carboxylic Acids

In a 500 ml 4-necked round-bottom flask equipped with stirrer, thermometer and reflux condenser, the alkyl urethane alkylene carboxylic acid methyl ester (for preparation see procedural step b) above, 1.0 molar equivalent) was mixed with water (6.2 g water per 1 g alkyl urethane alkylene carboxylic acid methyl ester) and sodium hydroxide solution (1.0 molar equivalent, 50% w/w NaOH in water) at room temperature. The mixture was stirred for 20 h at 20° C. and afterwards for 24 h at 50° C. Then, the mixture was allowed to cool to 20° C. and tert-butyl methyl ether (0.67 g tert-butyl methyl ether per 1 g water) was added, and the mixture was stirred for another 2 h at 20° C. The mixture was then gently warmed to 50° C. until the cloudy phases turned clear. The mixture was completely transferred into a separation funnel and phases were separated at 40° C. After separation, the aqueous phase was cooled to 5° C. and treated with concentrated hydrochloric acid (1.0 molar equivalent). The water was removed in a rotary evaporator at 80° C. and 10 hPa within 4 hours to yield the alkyl urethane alkylene carboxylic acids. The desired structure was confirmed by $^1$H-NMR in each case.

d) Synthesis of Alkyl Urethane Alkylene Carboxylate Ammonium Salts

In a 1000 ml 1-necked round-bottom flask the alkyl urethane alkylene carboxylic acid (for preparation see procedural step c) above; 1.0 molar equivalent) was mixed with ethanol (15.6.2 g ethanol per 1 g alkyl urethane alkylene carboxylic acid) and a solution of ammonia in ethanol (10 molar equivalents $NH_3$ of a 4% w/w solution of $NH_3$ in ethanol) at room temperature. The flask was fitted to a rotary evaporator and rotated for 30 min at 25° C. and 2 h at 60° C. The ethanol was gently removed at 60° C. and reduced pressure (30 to 200 hPa) within 4 hours. The crude ammonium salt was mixed with tert-butyl methyl ether (3 g tert-butyl methyl ether per 1 g crude ammonium salt) at 60° C. in an ultrasonic bath and then cooled to 20° C. The purified ammonium salt was filtered off and traces of tert-butyl methyl ether were removed by applying gently reduced pressure. The desired structure was confirmed by $^1$H-NMR in each case.

The following compounds of formula Ib were obtained according to the general procedure in the total yields as provided here below (% yield in relation to starting material used in procedural step a) or b), as given below):

Compound of formula III: 59% in relation to material used in procedural step b).

$^1$H-NMR of the compound of formula III in MeOD (tetramethylsilane, "TMS", as reference standard): δ =0.8-1.0 ppm (m, 6 H, 2×$CH_3$ of alkyl moiety), 1.1-1.6 ppm (m, 9 H, CH and $CH_2$ of alkyl moiety), 3.0-3.1 ppm (d, 2 H, $CH_2$ close to N of urethane group), 3.3 ppm (MeOH), 4.35-4.5 ppm (s, 2 H, $CH_2$ between carboxylate and urethane group), $NH_4$ and NH: broad signals Compound of formula IV: 37% in relation to material used in procedural step a).

$^1$H-NMR of compound of formula IV in MeOD (TMS): δ =0.8-1.0 ppm (m, 6 H, 2×$CH_3$ of alkyl moiety), 1.1-1.6 ppm (m, 13 H, CH and $CH_2$ of alkyl moiety), 3.0-3.1 ppm (d, 2 H, $CH_2$ close to N of urethane group), 3.3 ppm (MeOH), 4.35-4.5 ppm (s, 2 H, $CH_2$ between carboxylate and urethane group), $NH_4$ and NH: broad signals Compound of formula V: 43% in relation to material used in procedural step a).

$^1$H-NMR of compound of formula V in MeOD (TMS): δ =0.8-1.6 ppm (m, 25 H, $CH_2$ and $CH_3$ of alkyl moiety), 3.0-3.1 ppm (d, 2 H, $CH_2$ close to N of urethane group), 3.3 ppm (MeOH), 4.35-4.5 ppm (s, 2 H, $CH_2$ between carboxylate and urethane group), $NH_4$ and NH: broad signals Compound of formula VI: 18% in relation to material used in procedural step b).

$^1$H-NMR of compound of formula VI in MeOD (tetramethylsilane as reference standard): δ=0.8-1.0 ppm (t, 3 H, $CH_3$ of alkyl moiety), 1.1-1.6 ppm (m, 20 H, 10×$CH_2$ of alkyl moiety), 3.0-3.1 ppm (d, 2 H, $CH_2$ close to N of urethane group), 3.3 ppm (MeOH), 4.35-4.5 ppm (s, 2 H, $CH_2$ between carboxylate and urethane group), $NH_4$ and NH: broad signals.

Compound of formula VII: 51% in relation to material used in procedural step a).

Example 2: Synthesis of Comparative Compounds of Formulae X and XI a) Amidation

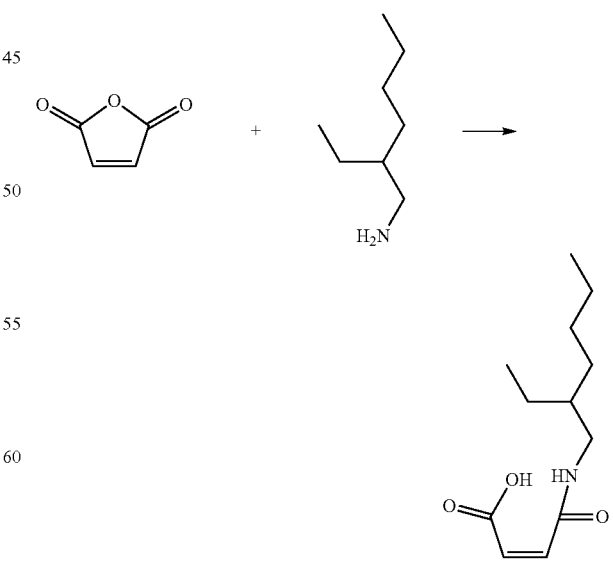

In a 250 ml 4-necked round-bottom flask equipped with stirrer, thermometer and reflux condenser, maleic acid anhydride (19.61 g, 0.20 mol, 1.0 molar equivalent) was dissolved in acetic acid (100 ml) and stirred at 25° C. Afterwards, 2-ethylhexylamine (25.85 g, 0.20 mol, 1.0 molar equivalent) was added dropwise over 2 h. Then, the resulting mixture was stirred and heated at 80° C. for 6 h and subsequently for 92 h at 25° C. The solvent was removed in a rotary evaporator at 80° C. and 10-20 hPa within 2 hours. 1 H-NMR of the crude product showed single formation of the desired amide ((2Z)-4-[(2-ethylhexyl)amino]-4-oxo-2-butenoic acid, CAS RN 6975-33-3).

b) Chlorination and Cyclisation

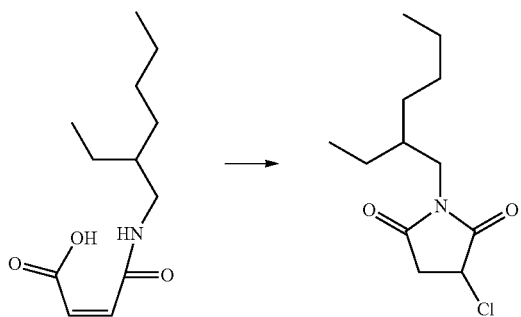 [SMILES: CCCCC(CC)CNC(=O)/C=C\C(=O)O ; CCCCC(CC)CN1C(=O)CC(Cl)C1=O]

In a 1000 ml 4-necked round-bottom flask equipped with stirrer, thermometer and reflux condenser, crude product from step a) (35.38 g, 0.156 mol, 1.0 molar equivalent) was dissolved in dichloromethane (500 ml) stirred at 10° C. N,N-dimethylformamide (0.19 g) was added. Afterwards, oxalyl chloride (21.93 g, 0.173 mol, 1.1 molar equivalent) was added dropwise over 45 min. Then, the resulting mixture was stirred and heated at 25° C. for 16 h and subsequently for 92 h at 25° C. The solvent was removed in a rotary evaporator at 80° C. and 10-20 hPa within 2 hours.

$^1$H-NMR of the crude mixture showed single formation of the desired chlorinated imide ("3-chloro-1-(2-ethylhexyl)pyrrolidine-2,5-dione").

c) Elimination

In a 1000 ml 4-necked round-bottom flask equipped with stirrer, thermometer and reflux condenser, crude product from step b) (37.5 g, 0.153 mol, 1.0 molar equivalent) was dissolved in dichloromethane (500 ml) stirred at 25° C. Afterwards, triethyl amine (23.16 g, 0.229 mol, 1.5 molar equivalent) was added at 25° C. dropwise over 15 min. Then, the resulting mixture was stirred at 25° C. for 24 h. The organic phase was extracted with aqueous solution of hydrochloric acid (2×500 ml of 1 N HCl in water). The organic phase was dried over magnesium sulfate, which was filtered off. The solvent was removed in a rotary evaporator at 50° C. and 10-20 hPa within 2 hours. $^1$H-NMR of the crude mixture showed single formation of the desired maleic acid imide (1-(-ethylhexyl)-1 H-pyrrole-2,5-dione; CAS RN 48149-71-9).

d) Diels-Alder Reaction

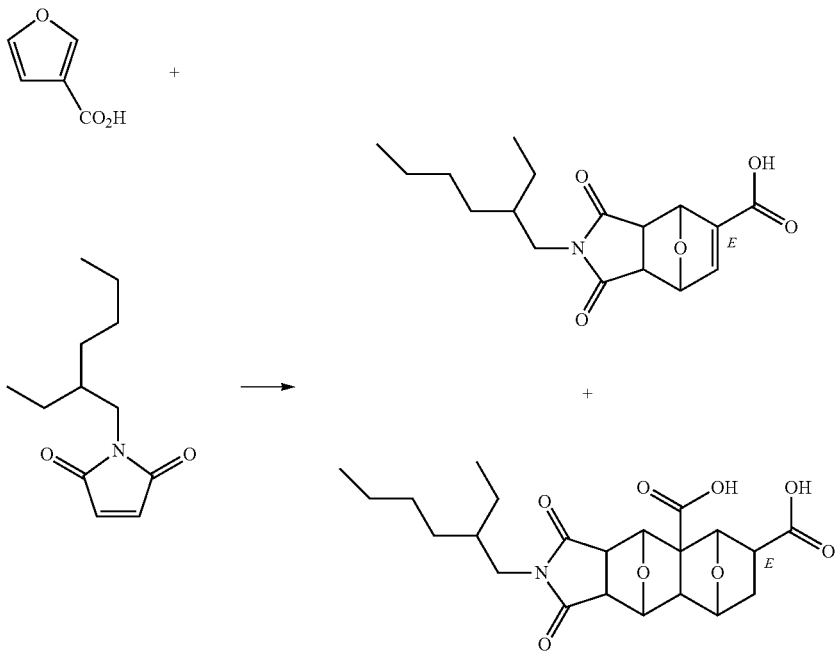

In a 250 ml 4-necked round-bottom flask equipped with stirrer, thermometer and reflux condenser, crude product from step c) (19.6 g, 0.094 mol, 1.0 molar equivalent) was mixed with 2-furane carboxylic acid (10.50 g, 0.094 mol, 1.0 molar equivalent) at 60° C. Then, the resulting mixture was stirred at 70° C. for 25.5 h. Afterwards, tert-butyl methyl ether (150 ml) was added at 25° C. and mixture was stirred for 1 h. Then, n-pentane (150 ml) was added and mixture was stirred for 1 h at 25° C. Small amounts of a precipitate are formed and filtered off. The solvent was removed in a rotary evaporator at 50° C. and 10-20 hPa within 2 hours. 18.3 g of product was isolated. $^1$H-NMR of the crude product confirmed formation of the Diels-Alder-adducts (mixture of 2 compounds, see reaction scheme above).

e) Neutralisation

In a 1000 ml 4-necked round-bottom flask equipped with stirrer, thermometer and reflux condenser, crude product from step d) (6 g) was dissolved in ethanol (20 ml) and stirred at 20° C. Then, 40 ml of NH$_4$OH in water (25 wt.-% in water) was added at 25° C. over 30 min. Then, the resulting mixture was diluted with methanol (500 g) and charcoal (10 g) was added. Charcoal was filtered off and the solvent was gently removed at 25° C. and at a pressure of <10 hPa. 6 g of a crude product was isolated. $^1$H-NMR of the crude mixture showed formation of the desired ammonia salts of the Diels-Alder adducts of formulae X and XI. The product was dissolved in water to obtain an aqueous solution with 15 wt.-% active content.

For the glass tube test (see example 3, below), the mixture of compounds of formulae X and XI was dried by removing the solvents (water and methanol) and the resulting solid was used in the test.

Example 3: Glass Tube Test

The following compounds were tested in example 3 ("test compounds"):

Compound of formula V according to the invention.

Mixture of compound of formula X (a Diels-Alder adduct):

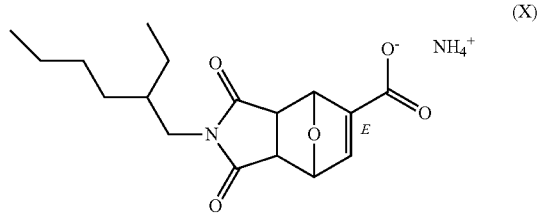 [SMILES: CCCCC(CC)CN1C(=O)C2C3C=C(C(=O)[O-])C(O3)C2C1=O ; [NH4+]]

(X)

and compound of formula XI (a Diels-Alder adduct):

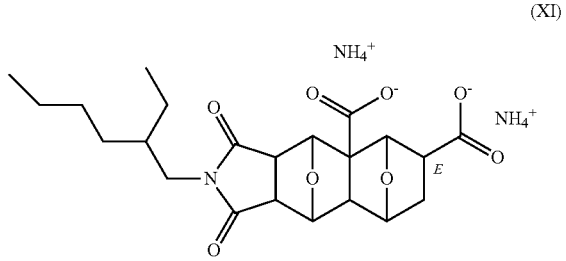 [SMILES: [NH4+] ; CCCCC(CC)CN1C(=O)C2C3OC(C2C1=O)C1(C(=O)[O-])C2OC(CC2C(=O)[O-])C31 ; [NH4+]]

(XI)

(not according to the invention) for comparison (for synthesis see example 2, above).

The total weight (mass) of an empty cylindrical quartz glass tube (length: 3 cm, diameter: 20 cm; not containing any test compound) was measured at room temperature. Then, the test compounds (1.35 g) were loaded into the quartz glass tube in each case and the total weight (mass) of the quartz glass tube filled with the test compounds was measured at room temperature. The quartz glass tube filled with a respective test compound was then evacuated to a pressure of 1 mbar (1 hPa) and heated to a temperature of 200° C. for 30 min. After cooling to room temperature, the total weight (mass) of the quartz glass tube (including the remainders/residuals from the test compounds or their fragments) was measured again.

The difference in weight (mass) of the quartz glass tube found after loading the test compound (mass of quartz glass tube plus test compound) and the weight (mass) of the quartz glass tube found after heating and evacuation (i.e. cleaving and removing of the test compound; mass of quartz glass tube plus remainders/residuals from the test compound or its fragments) was calculated and the results are shown in table 1 below in each case (i) as mass remaining of the test compounds after heating and evacuation and (ii) as mass percent remaining of the test compounds after heating and evacuation in relation to the total mass of test compound previously loaded to the quartz glass tube (differential measurement of masses).

TABLE 1

Test results from glass tube decomposition test

| Compound | Result |
| --- | --- |
| Compound of formula V (according to the invention) | 1 mg residual found after heating and evacuation (0.074 wt.-%) |
| Mixture of compound of formula X and compound of formula XI (comparison, not according to the invention) | 400 mg residual found after heating and evacuation (29.6 wt.-%) |

Example 4: Watermark Test

The following compounds (surfactants) were tested in example 4 ("test compounds"):

Compound of formula VII (according to the invention);

Linear dodecyl benzene sulfonate and Lutensol T08 (both not according to the invention) for comparison.

Four drops of a 0.5 g/L clear solution of the test compounds in water were dropped on the surface of a SiO$_2$ plate. The solution was allowed to dry and was then heated to 200° C. for 30 min.

After cooling to room temperature, it was found by visual inspection and photography that the residues of linear dodecyl benzene sulfonate (not according to the invention) and the residues of Lutensol T08 (not according to the invention) could not be evaporated without visible remainder from the surface of the SiO$_2$ μlate but that a ring of surfactant agglomerate remained on the plate's surface after heating.

In contrast, it was found by visual inspection that the compound of formula VII (according to the invention) could be evaporated without visible remainder from the surface of the SiO$_2$ μlate under the test conditions and that the plate's surface appeared free from visible residues after heating.

Example 5: Contact Angle Test

The compounds ("cleavable surfactants" of formula Ib according to the invention) shown in table 2 below were tested in example 5 ("test compounds").

Contact angles between a drop of pure water and the planar solid surface of a silicon wafer were measured according to the sessile drop method with the device OCA 200 from DataPhysics and Data Physics standard software, according to standard test method ASTM D7490-13.

About 10 µl of water were dropped from a syringe from a distance of about 0.5 cm onto the wafer's surface. As soon as the water droplet hit the surface, up to 200 pictures per second were taken by a high speed video camera. The contour of each droplet was analyzed and the contact angle, which is (as usual) the angle between the solid sample surface and the tangent of the droplet's shape at the edge of the droplet, was determined. The contact angel was recorded as function of time up to 100 seconds and provided as contact angle as measured after 10 s in table 2 below.

A silicon wafer was cleaned in aqueous HF (1% w/w in water) solution and rinsed with water followed by heating the wafer at 200° C. for 1 h. The resulting contact angle of water on the wafer's surface was found to be about 120° in all cases (see table 2: "pre-treatment value").

A test solution (0.5 g/L of the respective test compound in water, see table 2 below) and pure water (control) were adjusted to a pH value of 6.2, applied to the wafer's surface and the wafer's surface dried at room temperature in each case. The contact angle of water was then determined on the wafer's surface after this pre-treatment with the test solution and water. It was found that the contact angles of water determined at the positions on the wafer's surface where the test solution had been applied (and dried) showed reduced values (see table 2: "treatment value") when compared with the contact angle values of water determined at the positions where the pure water had been applied.

The silicon wafer was then heated to 200° C. for 30 min and cooled to room temperature again to remove the test compounds from its surface. The contact angle of water was then again determined at the positions as explained above (see table 2: "post-treatment value"). It was found that after the heat treatment, the contact angles of water determined at the positions on the wafer's surface where the test solution had been applied, nearly reached the pre-treatment values again. The results from the contact angle test are summarized in table 2 below:

TABLE 2

Results from contact angle test

| Test Compound or Control | Contact angle of water [°] - pre-treatment value | Contact angle of water [°] - treatment value | Contact angle of water - [°] post-treatment value |
| --- | --- | --- | --- |
| Water | 112 | 109 | 113 |
| Compound of formula III | 123 | 73 | 122 |
| Compound of formula IV | 117 | 77 | 119 |
| Compound of formula V | 119 | 29 | 108 |
| Compound of formula VII | 117 | 36 | 105 |

The results from example 5 show that the test compounds according to the invention ("cleavable surfactants") could be contacted with the surface of a silicon wafer for the purpose of treating or modifying, in particular cleaning or rinsing, the contacted surface and—after being cleaved by the trigger of heat (heating to a temperature of 200° C.) could be removed or completely removed again by evaporation.

The invention claimed is:

1. A method of cleaning and/or rinsing a semiconductor substrate, the method comprising:

making or providing a semiconductor substrate having at least one surface and having one or more materials on at least one of said at least one surface, contacting said one or more materials with an organic compound of the following formula I:

$$A\text{-}L\text{-}B \qquad (I),$$

or a salt thereof, wherein

A is a straight-chain or branched aliphatic hydrocarbon group having a total number of 4 to 20 carbon atoms, which is substituted by 1 to 4 ether groups, or is unsubstituted, B is a straight-chain or branched aliphatic hydrocarbon group having a total number of 1 to 6 carbon atoms, which is substituted by one or two ionic groups independently selected from the group consisting of anionic groups and cationic groups, and L is a urethane group, removing an amount of said compound of formula I or the salt thereof from said at least one surface, together with one or more of said one or more materials, to obtain a cleaned or rinsed semiconductor substrate having a residual amount of said compound of formula I or the salt thereof attached to at least one of said at least one surface, cleaving a fraction or total of said residual amount into a set of fragments by heating the fraction or total of said residual amount to a cleaving temperature at a cleaving pressure, each fragment having a boiling point below said cleaving temperature at the cleaving pressure applied, and removing said set of fragments from said at least one surface by evaporation.

2. The method of claim 1, wherein the removing of said set of fragments comprises evaporating said fragments at said cleaving temperature or at a temperature below said cleaving temperature and/or at said cleaving pressure or at a pressure below said cleaving pressure.

3. The method of claim 1, wherein, in said compound of formula I or the salt thereof, A is a monovalent group $R^1$—$CH_2$—, where $R^1$ is a straight-chain or branched aliphatic hydrocarbon group having a total number of 4 to 20 carbon atoms; and B is a monovalent ionic group of the following formula II

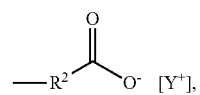

(II)

where $R^2$ is a straight-chain or branched aliphatic hydrocarbon group having a total number of 1 to 6 carbon atoms and $Y^+$ is a singly charged ammonium cation which is unsubstituted or substituted by 1 to 3 $C_1$-$C_4$-alkyl groups.

4. A method of making a semiconductor substrate, the method comprising:

making or providing a semiconductor substrate having at least one surface, contacting said at least one surface with an organic compound of the following formula (I):

A-L-B        (I), or a salt thereof, wherein

A is a straight-chain or branched aliphatic hydrocarbon group having a total number of 4 to 20 carbon atoms, which is substituted by 1 to 4 ether groups, or is unsubstituted, B is a straight-chain or branched aliphatic hydrocarbon group having a total number of 1 to 6 carbon atoms, which is substituted by one or two ionic groups independently selected from the group consisting of anionic groups and cationic groups, and L is a urethane group, so that said at least one surface is modified or treated, and subsequently cleaving said organic compound or the salt thereof on said at least one surface into a set of fragments.

5. The method of claim 4, wherein said contacting is conducted so as to achieve at least one effect selected from the group consisting of modifying by pore-sealing of low-k dielectric materials, repairing films of low-k dielectric materials, changing a zeta-potential of said at least one surface of an intermediate semiconductor substrate, changing a contact angle on said at least one surface of the intermediate semiconductor substrate, changing adsorption or adhesion properties of said at least one surface of the intermediate semiconductor substrate in relation to the compound of formula I and/or inhibiting corrosion; and treating by cleaning and/or rinsing;

and/or said cleaving comprises thermally cleaving said compound of formula I or the salt thereof on said at least one surface into the set of fragments, and/or removing said set of fragments from said at least one surface comprises evaporating the fragments.

6. The method of claim 4, wherein the compound of formula I or the salt thereof has a molecular weight not exceeding 1500 g/mol.

7. A compound of the following formula Ib,

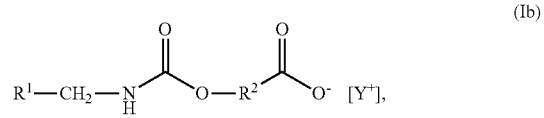

wherein $R^1$ is a straight-chain or branched aliphatic hydrocarbon group having a total number of 4 to 20 carbon atoms, $R^2$ is a straight-chain or branched aliphatic hydrocarbon group having a total number of 1 to 6 carbon atoms, and $Y^+$ is a singly charged ammonium cation which is unsubstituted or substituted by 1 to 3 $C_1$-$C_4$-alkyl groups.

8. The compound of claim 7, wherein $R^1$ is a straight-chain or branched aliphatic hydrocarbon group having a total number of 7 to 14 carbon atoms, $R^2$ is a straight-chain or branched aliphatic hydrocarbon group having a total number of 1 to 2 carbon atoms, and $Y^+$ is ammonium.

* * * * *